United States Patent
Assell et al.

(10) Patent No.: US 11,931,087 B2
(45) Date of Patent: Mar. 19, 2024

(54) BONE FRAGMENT AND TISSUE PROCESSING SYSTEM

(71) Applicants: ForCyte Medical, LLC, Marietta, GA (US); The Cleveland Clinic Foundation, Cleveland, OH (US)

(72) Inventors: Robert Assell, Minneapolis, MN (US); Andy Freeman, Minneapolis, MN (US); George Muschler, Cleveland Heights, OH (US)

(73) Assignees: ForCyte Medical, LLC, Marietta, GA (US); The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 17/741,828

(22) Filed: May 11, 2022

(65) Prior Publication Data
US 2023/0079824 A1 Mar. 16, 2023

Related U.S. Application Data

(63) Continuation of application No. 16/413,461, filed on May 15, 2019, now abandoned, which is a
(Continued)

(51) Int. Cl.
*A61B 17/88* (2006.01)
*A61B 17/00* (2006.01)
(Continued)

(52) U.S. Cl.
CPC ...... *A61B 17/8805* (2013.01); *A61B 17/1635* (2013.01); *A61B 17/8811* (2013.01);
(Continued)

(58) Field of Classification Search
CPC ............ A61B 17/8805; A61B 17/8811; A61B 17/1635; A61B 17/8833; A61B 17/1615;
(Continued)

(56) References Cited

U.S. PATENT DOCUMENTS

| 5,269,785 A | * | 12/1993 | Bonutti | ............... A61B 17/1635 606/80 |
| 5,624,418 A | * | 4/1997 | Shepard | .................. A61M 1/79 604/319 |

(Continued)

*Primary Examiner* — Benjamin J Klein
*Assistant Examiner* — Gabriella E Burnette
(74) *Attorney, Agent, or Firm* — Spencer Fane, LLP

(57) ABSTRACT

A tissue collection and processing system for collecting bone fragments and tissue aspirated from a bone. The tissue collection and processing system includes a collection vessel, a collection vessel cap, a processing piston, a first tubing and a fluid withdrawal mechanism. The collection vessel has an opening formed therein to receive bone fragments and tissue aspirated from the bone. The collection vessel cap is capable of engaging the collection vessel to substantially seal the opening. The collection vessel cap or the collection vessel has a first port. The processing piston has an upper surface and a lower surface. The processing piston has a connection port and a bore. The connection port is proximate the upper surface. The bore is fluidly connected to the connection port and extends toward the lower surface. The processing piston has a density that is less than a density of fluid in the aspirated bone fragments and tissue. The fluid withdrawal mechanism is fluidly connected to the connection port with the first tubing to withdraw the fluid from the collection vessel. As fluid is withdrawn from the collection vessel, the processing piston is slidable in the collection vessel.

18 Claims, 11 Drawing Sheets

Related U.S. Application Data continuation-in-part of application No. 15/150,089, filed on May 9, 2016, now Pat. No. 10,342,552.

(60) Provisional application No. 62/193,451, filed on Jul. 16, 2015, provisional application No. 62/158,574, filed on May 8, 2015.

(51) Int. Cl.
| | | |
|---|---|---|
| *A61B 17/16* | (2006.01) | |
| *A61J 1/14* | (2023.01) | |
| *A61J 1/20* | (2006.01) | |
| *A61L 27/36* | (2006.01) | |
| *A61M 1/00* | (2006.01) | |
| *C12M 1/26* | (2006.01) | |
| *A61L 27/38* | (2006.01) | |

(52) U.S. Cl.
CPC ......... *A61B 17/8833* (2013.01); *A61J 1/1475* (2013.01); *A61J 1/2086* (2015.05); *A61L 27/3608* (2013.01); *A61L 27/3691* (2013.01); *A61M 1/63* (2021.05); *A61M 1/79* (2021.05); *A61M 1/815* (2021.05); *A61B 2017/00561* (2013.01); *A61B 2017/00969* (2013.01); *A61B 17/1615* (2013.01); *A61J 1/2058* (2015.05); *A61L 27/3834* (2013.01); *A61L 2430/02* (2013.01); *C12M 33/04* (2013.01)

(58) Field of Classification Search
CPC ........... A61B 2017/00969; A61B 2017/00561; A61M 1/63; A61M 1/79; A61M 1/815; A61M 2205/7545; A61J 1/1475; A61J 1/2086; A61J 1/2058; A61L 27/3608; A61L 27/3691; A61L 27/3834; A61L 2430/02; C12M 33/04; A61F 2/4601
See application file for complete search history.

(56) References Cited

U.S. PATENT DOCUMENTS

| | | | |
|---|---|---|---|
| 2006/0273049 A1* | 12/2006 | Leach | B01L 3/50215 210/787 |
| 2008/0283474 A1* | 11/2008 | Leach | A61M 1/029 210/789 |
| 2009/0014391 A1* | 1/2009 | Leach | A61M 1/3693 210/740 |
| 2009/0287190 A1* | 11/2009 | Shippert | A61M 1/79 604/542 |
| 2014/0323914 A1* | 10/2014 | VanderWoude | A61M 1/91 600/582 |
| 2015/0110890 A1* | 4/2015 | Assell | A61L 27/365 424/549 |
| 2015/0273360 A1* | 10/2015 | King | G01N 33/491 210/800 |

* cited by examiner

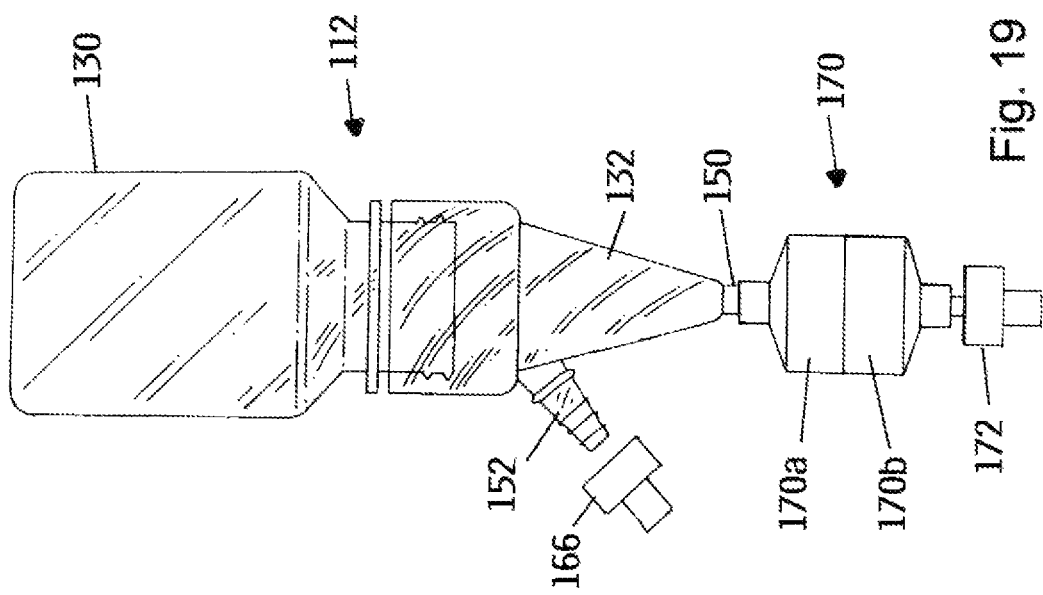
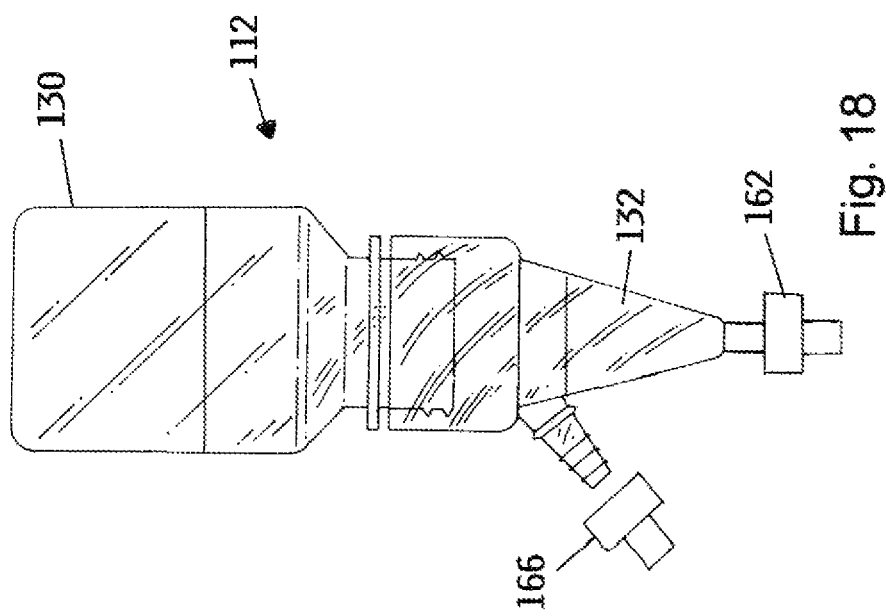

BONE FRAGMENT AND TISSUE PROCESSING SYSTEM

REFERENCE TO RELATED APPLICATION

This application is a continuation of U.S. application Ser. No. 16/413,461, filed May 15, 2019, which is a continuation-in-part of U.S. application Ser. No. 15/150,089, filed May 9, 2016, which claims priority to Provisional Applic. No. 62/193,451, filed on Jul. 16, 2015 and Provisional Applic. No. 62/158,574, filed on May 8, 2015, the contents of which are incorporated herein by reference.

FIELD OF THE INVENTION

The invention relates generally to collection and processing of bone fragments and tissue that may be used in preparing bone void fillers. More particularly, the invention relates to bone fragment and tissue processing system.

BACKGROUND OF THE INVENTION

In the US, bone grafts are most commonly used in spinal fusion surgery and, more generally, in the fusion or arthrodesis of any skeletal joint. In addition, bone graft is generally used in trauma surgery for the treatment of fresh fractures and non-unions, which are typically identified as fractures within 6 months that have not healed properly. The bone graft materials typically bridge a gap between bone segments and may also provide a three-dimensional scaffold on which the bone can grow.

Bone graft treatment is also typically used in conjunction with fresh fractures where the bone has been shattered or where the patient is at a very high risk of developing a non-union fracture. Because many fractures are not this severe and can be treated with alternative methods of fixation, bone grafts are not frequently needed during fresh fracture treatments.

Two areas where bone grafts are used is in conjunction with joint reconstruction and joint revision. For example, the bone graft may be used to fill a void between the bone and joint implant in a joint reconstruction surgery. Joint revision is much more likely to need a bone graft because a large void may result from the removal of the original implant. Joint revisions that use bone graft material therefore usually require a relatively large quantity of the bone graft material.

There are different types of bone graft materials that may be used to assist a patient's body in bone regeneration. These bone graft materials are typically classified as either natural or synthetic materials.

Natural bone graft materials are classified in the following groups. Autograft is bone graft material that is obtained from the same individual that will receive the bone graft material. Allograft is bone graft material that is obtained from another human source, which typically is from cadavers. Xeongraft is bone graft material that is obtained from another species.

Bone grafts can also be categorized by their bone-forming properties as osteoconductive, osteoinductive or osteogenic. Osteoconductivity is the ability of a material to provide an appropriate scaffold or matrix upon which new bone tissue can form. Osteoinductivity is the ability of a material to stimulate the patient's own system to form new bone. Osteogenic material generates new bone tissue itself. Osteoblasts, which can be found in bone marrow and mesenchymal cells, are the only cells that can create new bone.

Autograft bone has historically been the standard of care because of its osteoconductive, osteoinductive and osteogenic properties. At the time of surgery, bone is taken from a donor site in the patient, often the iliac crest bone but others are used, and then is re-implanted back into the patient at the surgical site.

Autograft is often not used, because obtaining the graft generally requires a second surgical procedure with associated risks and expenses. The autograft also typically results in significant post-operative issues, most significantly pain. An additional type of autograft, concentrated cells from bodily fluids such as blood or bone marrow, is often used as well.

In addition to autograft, many other types of bone graft are used including processed cadaver bone, i.e., allograft, in the form of demineralized bone matrix and also so called "living cell" or "stem cell" allograft. Additionally, constituents know to be involved in new bone formation, such as bone morphogenic proteins, typically produced by recombinant processing means, as used. Synthetic materials such as tri-calcium phosphate, calcium sulphate, hydroxyapatite and others are used as well.

| Summary of Bone Graft Characteristics by Material | | | |
|---|---|---|---|
| Type | Osteoconductive | Osteoinductive | Osteogenic |
| Autograft | Yes | Yes | Yes |
| Bone morphogenic proteins | No | Yes (strong) | No |
| Demineralized bone matrix | Yes | Minimal | No |
| Allogeneic stem cell | Yes | Unknown | Yes |
| Bone marrow aspirate | No | Yes (strong) | Yes |
| Synthetics | Yes | No | No |

Bone graft substitutes also fall within the classification of bone filler materials. Examples of bone graft substitutes include collagen, polymers such as silicone and some acrylics, hydroxyapatite, calcium sulfate and ceramics.

Bone cement (such as polymethylmethacylate) can be used as a bone void filler to treat bone voids or defects. For example, it can be used to repair fractured bones and vertebral bodies. The bone cement can be used either in procedures that involve direct injection of the bone cement into the fractured vertebral body (i.e., vertebroplasty) or injection of the bone cement into the vertebral body after the height of the vertebral body is restored using a pressurized balloon (i.e., kyphoplasty).

One of the disadvantages of using bone cement is that, once it is injected inside the patient, the bone cement is an inorganic material and, as such, is treated as a foreign body. As such, the bone cement may not only negatively impact healing but can also lead to bone disease.

Additionally, the bone cement is typically stiffer than bone, which may increase the incidence of adjacent level fractures in the spine. Bone cement leakage may cause complications, and has been reported to occur in vertebroplasty and kyphoplasty procedures. If leakage does occur, the bone cement can cause soft tissue injury due to the high temperatures of the exothermic polymerization reaction. In addition, if the bone cement is forced into the vascular system, it can cause emboli.

Bone marrow and bone marrow aspirate concentrate are considered to have a significantly higher bioactivity than circulating blood or concentrated blood known as platelet rich plasma. These features mean that bone marrow is often viewed as being superior to platelet rich plasma for use in orthopedic applications such as spinal fusion and trauma surgery because the bone marrow contains progenitor cells and multipotent stem cells, which assist in the formation of new bone.

Bone marrow aspirate concentrate has become increasingly popular in bone growth applications, particularly spinal fusion and trauma surgery, because of its osteogenic properties. Traditionally, autograft was the gold standard grafting material in these procedures due to the presence of osteoblasts and osteogenic precursor cells, as well as its osteoconductive and osteoinductive properties.

To avoid the risks associated with autograft procurement such as donor site infection and morbidity, bone marrow aspirate concentrate has been increasingly used because it has properties that are similar to autograft and allows surgeons and patients to avoid autograft procurement.

Muschler, U.S. Pat. Nos. 5,824,084 and 6,049,026, both disclose systems for preparing bone graft in which a bone marrow suspension is passed through a porous, biocompatible implantable matrix. Muschler indicates that the bone graft can be prepared intra operatively for use in a person from which the bone graft aspirate was obtained.

Muschler, U.S. Pat. No. 6,723,131, discloses a system for preparing bone graft. A porous, biocompatible implantable matrix is placed in a hollow column having caps at opposite ends. Bone marrow aspirate is placed in a syringe, which is attached to one of the caps, and then the syringe is used to urge the bone marrow aspirate through the porous, biocompatible implantable matrix.

SUMMARY OF THE INVENTION

An embodiment of the invention is directed to a tissue collection and processing system for collecting bone fragments and tissue aspirated from a bone. The tissue collection and processing system includes a collection vessel, a collection vessel cap, a processing piston, a first tubing and a fluid withdrawal mechanism. The collection vessel has an opening formed therein to receive bone fragments and tissue aspirated from the bone. The collection vessel cap is capable of engaging the collection vessel to substantially seal the opening. The collection vessel cap or the collection vessel has a first port. The processing piston has an upper surface and a lower surface. The processing piston has a connection port and a bore. The connection port is proximate the upper surface. The bore is fluidly connected to the connection port and extends toward the lower surface. The processing piston has a density that is less than a density of fluid in the aspirated bone fragments and tissue. The fluid withdrawal mechanism is fluidly connected to the connection port with the first tubing to withdraw the fluid from the collection vessel. As fluid is withdrawn from the collection vessel, the processing piston is slidable in the collection vessel.

Another embodiment of the invention is directed to a tissue collection and processing system for collecting bone fragments and tissue aspirated from a bone. The tissue collection and processing system includes a collection vessel, a collection vessel cap, a bone fragment and tissue harvesting device, a first tubing and a filter mechanism. The collection vessel has an opening formed therein. The collection vessel cap is capable of engaging the collection vessel to substantially seal the opening. The collection vessel cap or the collection vessel has a first port. The bone fragment and tissue harvesting device is capable of aspirating bone fragments and tissue from a bone. The filter container is mounted with respect to the first port. The first tubing fluidly connects the bone fragment and tissue harvesting device to the first port so that a portion of the bone fragments and tissue in the aspirated bone fragments that are not retained in the filter container accumulate in the collection vessel.

Another embodiment of the invention is directed to a method of collecting and processing bone fragments and tissue aspirated from a bone. A collection vessel, a collection vessel cap and a filter container are provided. The collection vessel has an opening formed therein. The collection vessel or the collection vessel cap has a first port. The filter container is mounted with respect to the first port. The collection vessel cap is attached to the collection vessel to substantially seal the opening. The first port is connected to a bone fragment and tissue harvesting device with a first tubing. Bone fragments and tissue are aspirated from a bone with the bone fragment and tissue harvesting device. A portion of the bone fragments and tissue is retained in the filter container. The aspirated bone fragments and tissue that is not retained in the filter container are accumulated in the collection vessel.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 18 is a side view of the osteomedullary tissue collection and processing device in an inverted position for separating the coagulated red blood cells from the aspirated tissue.

FIG. 19 is a side view of the osteomedullary tissue collection and processing device attached to a mixing device containing porous, biocompatible implantable matrix.

DETAILED DESCRIPTION OF THE INVENTION

Figure 1:
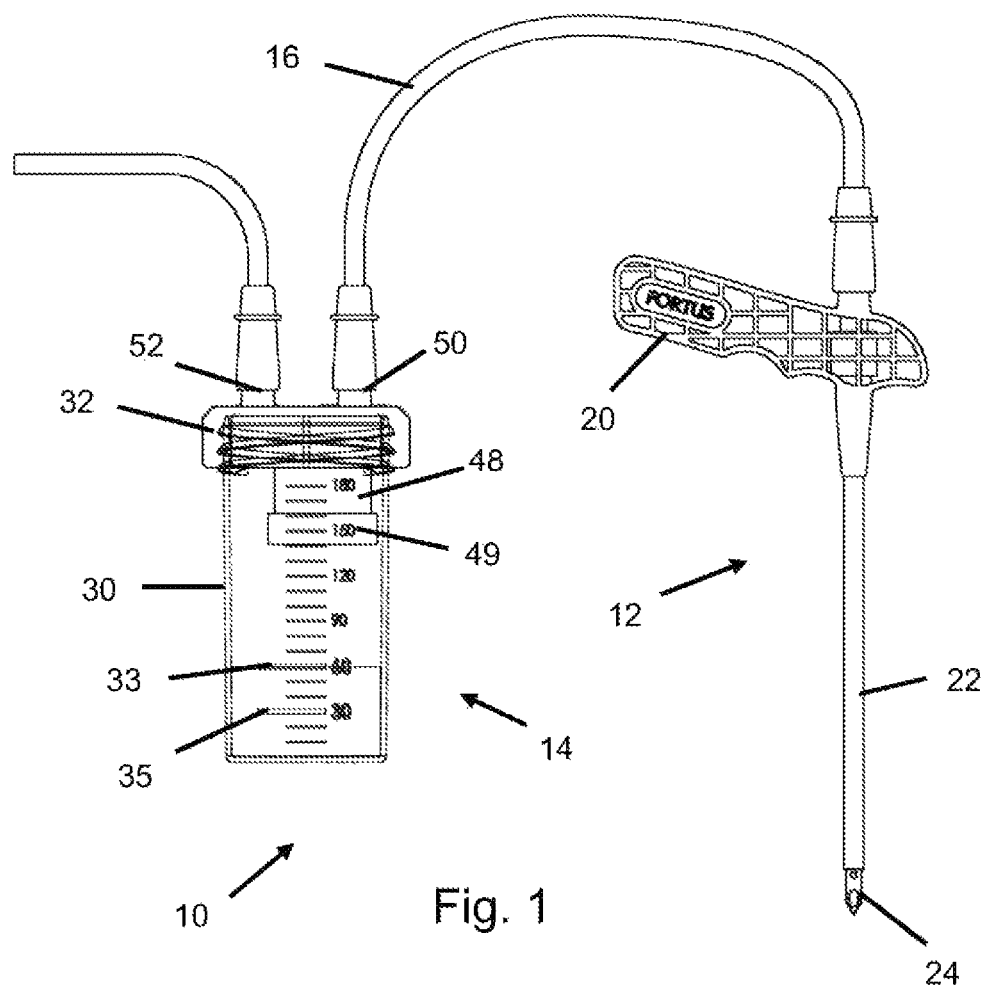
FIG. 1 is a side view of a bone fragment and tissue harvesting and processing system according to an embodiment of the invention.

An embodiment of the invention is directed to a bone fragment and tissue harvesting and processing system, which is illustrated in FIG. 1. The bone fragment and tissue harvesting and processing system 10 generally includes a harvesting device 12 that is operably attached to a processing device 14 with tubing 16.

A significant advantage of the invention is that it is a contained system, which facilitates use of the invention in an operating room as well as in an out-patient setting. The invention thereby enables high-quality bone grafts to be prepared in a cost-effect manner proximate to when it is desired to use the bone graft.

The bone fragment and tissue harvesting and processing system 10 facilitates extraction of bone fragments and tissue from a patient that are then used in preparing a bone graft, as is described in more detail herein.

The terms bone fragments and tissue, as used herein, are intended to be broadly construed to encompass all aspiratable components within the bone regardless of the nature of such components.

The invention thereby provides a completely autologous process that enables use of the patient's own tissue in preparing a bone graft. In addition to harvesting bone fragments, the invention enables high yield harvesting of stem and progenitor cells as well as collection of intramedullary bone graft in a process that is safe, fast and efficient. This tissue is used in conjunction with an osteoconductive matrix to form a bone graft.

The harvesting device 12 includes a handle portion 20 and a needle portion 22 that are operably connected to each other. In certain embodiments, the needle portion 22 is detachably connected to the handle portion 20. In other embodiments, the needle portion 22 is integrally formed with the handle portion 20.

In certain embodiments, the needle portion 22 may have an outer diameter of about 6 millimeters. Forming the needle portion with this diameter minimizes the potential that bone fragments will become stuck while being drawn through the needle portion 20 during the aspiration process.

The needle portion 22 having the preceding characteristics may have a two-part configuration. An inner portion of the needle portion 22 may include an inner shaft and an outer shaft. The inner shaft may be fabricated from a metallic material such as stainless steel. The metallic material thereby provides the needle portion 22 with a relatively high strength while having a relatively thin wall thickness. In certain embodiments, the wall thickness of the metallic material may be less than about 10 thousandths of an inch. In certain embodiments, the wall thickness of the inner shaft is between about 3 and 6 thousandths of an inch. In still other embodiments, the wall thickness of the inner shaft is about 4 thousandths of an inch.

Fabricating the inner shaft with a relatively thin wall thickness allows the inner channel to be relatively wide to facilitate a large flow rate of bone fragments and tissue therethrough while at the same time having a relatively small outer diameter to minimize the size of the hole that is formed in the bone to access the interior of the bone where the bone fragments are formed and the beneficial tissue is located.

The outer shaft may be fabricated from a polymeric material that is molded over the inner shaft. The outer shaft thereby enhances strength of the inner shaft while allowing the needle to deflect during the bone marrow and tissue harvesting process. The combined structure of the inner shaft and the outer shaft provides the needle portion 22 with enhanced torsional strength compared to a needle fabricated only from a metallic material or a polymeric material.

To provide the needle portion 22 with a desired level of sharpness, the needle portion 22 has a tip that is fabricated from a metallic material as the metallic material provides an enhanced sharpness as compared to a tip 24 fabricated from a polymeric material. The tip 24 may be attached to the distal end of the inner tube before the outer tube is molded over the inner tube.

Another advantage of using the polymeric outer shaft over the metallic inner shaft is that it is possible for the bore that extends through the inner shaft to be relatively constant over the length of the needle portion 22. If the needle portion 22 had been fabricated only from a polymeric material, it would have been necessary for the inner diameter to taper when moving from the proximal end to the distal end of the needle portion 22 to facilitate molding of the needle portion 22. Because of the length of the needle portion 22, such tapering would have resulted in a relatively thick wall proximate the proximal end, a relatively thin wall proximate the distal end or combination thereof. Such differences in wall thickness would have limited the flexing of the needle portion 22 near the proximal end while providing too much flexibility proximate the distal end. Both of these situations would have limited the ability to maneuver the needle during the bone fragment and tissue recovery process.

Figure 2:
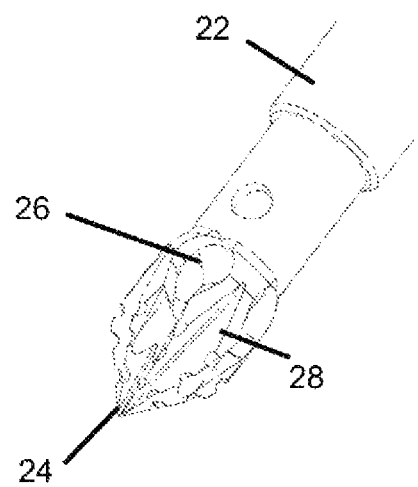
FIG. 2 is a perspective view of a needle for use in conjunction with the bone fragment and tissue harvesting and processing system of FIG. 1.

The sharpened tip 24, which is most clearly illustrated in FIG. 2, that facilitates accessing the interior of a bone. Thereafter, the harvesting device 12 may be manipulated to form bone fragments. The harvesting device 12 also facilitates morselizing tissue inside of the bone and thereby enhances the amount of osteomedullary tissue that can be recovered from a patient. The bone fragments and tissue are aspirated from the patient using the harvesting device 12, which causes the aspirated tissue to be collected in the processing device 14.

Because there are a relatively large concentration of bone fragments that are aspirated through the harvesting device 12, the tip 24 of the needle portion 22 includes a plurality of relatively large apertures 26 formed therein proximate the distal end thereof. Intermediate the apertures 26 is at least one sharpened surface 28. The at least one sharpened surface 28 facilitates cutting while the needle portion 22 is inserted into and removed from the bone. The at least one sharpened surface 28 also facilitates cutting while the needle portion 22 is axially rotated and/or pivoted.

The processing device 14 generally includes a collection vessel 30 to which a collection vessel cap 32 is operably attached. The collection vessel 30 may be formed with a size based upon the volume of bone fragments and tissue that is anticipated to be aspirated from the patient. In certain embodiments, the collection vessel 30 has a volume of about 180 millimeters.

The collection vessel 30 may have a variety of shapes using the concepts of the invention. In certain embodiments, the collection vessel 30 has a generally cylindrical shape. Using such a shape enables the collection vessel cap 32 to be attached using a rotational motion.

A side of the collection vessel 30 may include at least two volume collected markers 33, 35. In one embodiment, the volume collected markers include an upper marker 33 and a lower marker 35. The upper marker 33 and the lower marker 35 thereby provide guidance to the person using the invention regarding whether a desired volume of tissue has been collected. In other embodiments, the volume collected markers may include a series of identifiers that correspond to a conventional volume measuring system such as milliliters.

Proximate an upper end of the collection vessel 30, an opening 34 may be provided. In one such embodiment, the opening 34 is generally circular and has a thread on a surface thereof that can be used when attaching the collection vessel cap 32 to the collection vessel 30. In certain embodiments, the thread may be on an outer surface of the opening 34. A person of skill in the art will appreciate that a variety of other techniques may be used to attach the collection vessel cap 32 to the collection vessel 30.

One aspect of the attachment of the collection vessel cap 32 to the collection vessel 30 is that a substantially air-tight seal is formed when the collection vessel cap 32 is attached to the collection vessel 30 so that a vacuum may be used to draw the aspirated bone fragments and tissue into the collection vessel 30.

The collection vessel 30 may be fabricated from a variety of materials using the concepts of the invention. In one embodiment, at least a portion of the collection vessel 30 is fabricated from a transparent material. Such a configuration enables a person using the bone fragment and tissue harvesting and processing system 10 to not only view the volume of aspirated tissue in the collection vessel 30 but also other characteristics of the aspirated tissue such as a color of the aspirated tissue and/or the presence of discrete regions in the aspirated tissue.

Another criterion for the material that is used in fabricating the collection vessel 30 is that the material be biologically compatible and facilitate sterilization of the collection vessel 30 prior to use. An example of one such material that may be used to fabricate the collection vessel 30 is polyethylene terephthalate.

The collection vessel cap 32 may have a generally cylindrical configuration with an inner diameter that is selected based upon an outer diameter of the collection vessel 30 proximate the threaded region to facilitate removable attachment of the collection vessel cap 32 to the collection vessel 30. In this regard, the collection vessel cap 32 may include a thread on an inner surface thereof that is shaped generally complementary to the thread on the collection vessel 30.

While not illustrated, at least a portion of the outer surface of the collection vessel cap 32 may have a shape and/or texture that enhances the ability to grasp the collection vessel cap 32 and turn the collection vessel cap 32 with respect to the collection vessel 30. Because of the nature of the invention and the potential desire to remove the collection vessel cap 32, the collection vessel cap 32 is typically intended to be tightened and loosened using manual force.

The collection vessel cap 32 includes a first port 50 and a second port 52 formed therein. A person of skill in the art will appreciate that at least one of the first port 50 and the second port 52 may alternatively be formed in the collection vessel 30.

The first port 50 includes a connector that facilitates attachment to the tubing 16. In certain embodiments, the first port 50 enables tubing to be attached and detached. When the tubing is attached, a substantially gas-impervious seal is formed. The first port 50 may include a standardized connector profile that enables a variety of objects to be attached thereto. An example of one suitable standardized connector is marketed under the identifier Leur Lock.

Similar to the first port 50, the second port 52 may be formed with a standardized connector profile. An example of one such connector profile that can be used for the second port 52 is a tapered push-on connector that facilitates a friction connection. In such embodiments, the push-on connector includes a plurality of ridges, which reduce the potential of the tubing or other object becoming detached from the second port 52.

The collection vessel cap 32 may be fabricated from a variety of materials using the concepts of the invention. In one embodiment, at least a portion of the collection vessel cap 32 is fabricated from a transparent material.

Another criterion for the material that is used in fabricating the collection vessel cap 32 is that the material be biologically compatible and facilitate sterilization of the collection vessel cap 32 prior to use. An example of one such material that may be used to fabricate the collection vessel cap 32 is polyethylene terephthalate.

A filter container 48 is provided in the processing device 14. The filter container 48 is positioned so that as the bone fragments and tissue flow through the first port 50, these components pass through the filter container 48. In certain embodiments, the filter container 48 is attached to an inner surface of the collection vessel cap 32. The filter container 48 may be removably attached to the collection vessel cap 32 such as using a threaded mechanism.

In other embodiments, the filter container 48 may be attached to an outer surface of the collection vessel cap 32. In such an embodiment, the first port 50 may be directly attached to the filter container 48. In still other embodiments, the filter container 48 may be separate from the processing device 14. In this configuration, the tubing 16 is attached to the filter container 48. Another section of tubing (not shown) attached the filter container outlet to the first port 50.

The filter container 48 may have a volume that is significantly smaller than the volume of the processing device 14. In certain embodiments, the filter container 48 has a volume of less than about 20 cubic centimeters. In other embodiments, the volume of the filter container 48 is about 15 cubic centimeters.

A surface of the filter container may have perforations formed therein. In certain embodiments, a lower surface 49 of the filter container 48 may be perforated having a plurality of openings formed therein. The size of the openings may be selected to retain substantially all of the bone fragments in the filter container 48 as the bone fragments and tissue are aspirated from the patient. On the other hand, the openings are sufficiently large so that the liquid in the aspirated is permitted to flow through the lower surface 49 and into the collection vessel 30. The perforations thereby affect physical separation of the aspirate.

In certain embodiments, the lower surface 49 is integrally formed with the other components of the filter container 48. In other embodiments, the lower surface 49 may be removably attached to the filter container 48 such as using a threaded mechanism. This threaded mechanism may be similar to the threaded mechanism that is used to attach the filter container 48 to the collection vessel cap 32.

A filter material at least partially fills the filter container 48. The filter material is selected with a pore size such that substantially all of the bone fragments are retained in the filter material. The filter material may also be selected to retain at least a portion of the beneficial cells in the tissue. In certain embodiments, the filter material retains substantially all of progenitor cells in the extracted tissue.

The filter material may thereby provide physical separation of the bone fragments from the remainder of the material in the aspirate. Such a separation mechanism is referred to as physical separation. The filter material may also have an affinity for the beneficial components in the aspirate such that as the beneficial components flow past the filter material, the beneficial components are attached to the filter material so that the beneficial components retained in the filter container 48 would be included in the bone graft fabricated therefrom.

As an alternative to providing a relatively homogeneous filter material in the filter container 48, it is possible for the filter material to include more than one region. For example, there may be a top filter material portion and a bottom filter material portion. The top filter material portion may have a predisposition for retaining the bone fragments therein. The bottom filter material portion may have a predisposition for retaining the beneficial portions of the tissue therein.

In addition to or as an alternate to the filter material described above, the filter container 48 may have a filter membrane that is fabricated with a pore size that retains a desired portion of the bone fragments and the tissue within the filter container 48. For example, forming the filter membrane with a pore size of between about 20 microns and about 100 microns would facilitate retaining the bone fragments and a substantial portion of the progenitor cells in the filter container 48.

In yet another configuration, the filter container 48 is selected to retain the bone fragments therein but substantially all of the remainder of the tissue flows into the collection vessel 30. The tissue in the collection vessel 30 may thereby include in addition to progenitor cells, red blood cells and other components that are not needed or potentially detrimental to forming the bone void filler. In such a situation, the red blood cells may be caused to separate from the remainder of the tissue such as mixing a material that causes the red blood cells to agglomerate and settle to the bottom of the collection vessel 30. More details on such a process are described later in this application.

Because of the challenges in aspirating the tissue that is collected in the collection vessel 30, it is desirable for substantially all of the tissue to be retained in the collection vessel 30 for further processing. To reduce the potential of loss of the aspirated tissue that is collected in the bone fragment and tissue harvesting and processing system 10, a hydrophilic membrane valve (not shown) may be attached to the second port 52 intermediate the processing device 14 and the vacuum source.

The hydrophilic membrane valve allows the vacuum to pull gas therethrough until the hydrophilic membrane becomes wet such as when the bone fragment and tissue harvesting and processing system 10 is knocked over or the bone fragment and tissue harvesting and processing system 10 is overfilled with liquid. The hydrophilic membrane valve thereby prevents the aspirated tissue from being drawn out of the bone fragment and tissue harvesting and processing system 10.

To minimize the potential of the processing device 14 being moved from a vertical orientation, the processing device 14 may be placed in a base (not shown) having a width that is greater than the width of the processing device 14. An example of one suitable technique that may be used to retain the processing device 14 in a vertical orientation is described herein.

An alternative or additional technique to minimize the potential of aspirated tissue being drawn into the vacuum line may include attaching the processing device 14 to an object proximate to the patient from which the tissue is being aspirated. An example of one suitable option is a clip that attaches the processing device 14 to an IV pole, a drape near the patient or the operating table.

Prior to use, the components of the bone fragment and tissue harvesting and processing system 10 may be sterilized. A person of skill in the art will appreciate that a variety of sterilization techniques may be used. An example of one suitable sterilization technique is exposure of the packaged components to gamma radiation.

As an initial step in harvesting the bone fragments and tissue, the collection vessel cap 32 is attached to the collection vessel 30 so that the bone fragment and tissue harvesting and processing system 10 looks substantially as illustrated in FIG. 1. The tissue harvesting device 12 is attached to the processing device 14 using the tubing 16. A vacuum source is attached to the second port 52.

A site is selected from which the bone fragments and tissue are to be harvested. It is possible to use the invention in conjunction with harvesting bone fragments and tissue from a variety of bones in a patient. Preferred sites for harvesting the bone fragments and tissue include the iliac crest and pedicle/vertebral bodies.

During the process of extracting the bone fragments and tissue, the needle portion 22 is partially withdrawn and then reinserted in a different direction. Such a process increases the amount of bone fragments and osteomedullary tissue that is harvested from the patient. Using such a process it is desirable for the needle to flex but at the same time not break or remain in a deformed/deflected configuration.

During the aspiration process it is important for the relatively liquidy morselized tissue to be aspirated along with the bone fragments. Such a process minimizes the potential of the bone fragments becoming stuck while passing through the harvesting device 12 and the tubing 16 before reaching the collection vessel.

The aspiration process thereby depends on the formation of relatively small bone fragments, which is primarily caused by contact between the needle tip 24 and the harder areas inside the bone. The movement of the needle tip 24 through the interior of the bone also causes morselizing of the tissue inside the bone and such morselizing causes the tissues to become more liquidy.

To enhance the volume of bone fragments and tissue that can be aspirated, the needle portion 22 may be rotated as the distal end of the needle portion 22 moves through the interior of the bone. Such movement causes bone fragments to be formed. The movement also causes morselizing of the tissue inside of the bone, which enhances the ability to withdraw the tissue. This process significantly increases the volume of beneficial bone fragments and tissue that can be harvested as compared to conventional processing techniques that merely insert the aspiration needle into the bone at different depths.

A vacuum is applied to the system, which causes the bone fragments and tissue to be aspirated through the needle portion 22. The aspirated bone fragments and tissue flow through the tubing 16 and into the processing device 14. This process is continued until a desired volume of osteomedullary tissue has been aspirated from the patient.

Thereafter, the bone fragments and tissue pass through the filter material in the filter container 48, which retains the bone fragments and at least a portion of the beneficial portions of the tissue therein. Depending on the intended use of the bone void filler, it may be possible to directly use the material in the filter container 48. Alternatively, it is possible to mix additional components to fabricate the bone void filler.

If it is not possible to obtain a desired volume of the bone fragments and tissue from a particular location, it may be necessary to insert the needle portion 22 into a different location in the bone. It may also be necessary to insert the needle portion 22 into a different bone.

It may be desirable to control the intensity of the vacuum that is pulled through the harvesting device 12. An example of one mechanism to control the vacuum level is using a valve that is operably attached to the vacuum line that is attached to the first port 50.

It is possible to further process the aspirate that is collected in the collection vessel 30 to recover beneficial components therefrom. Such further processing may utilize a processing piston that is slidably positioned within the collection vessel 30 similar to the processing piston 42 that is described herein with respect to the embodiment illustrated in FIGS. 3-7. This separation may utilize a red blood cell clotting material to separate the red blood cells from the beneficial components of the aspirate that remain in the collection vessel 30.

Figure 3:
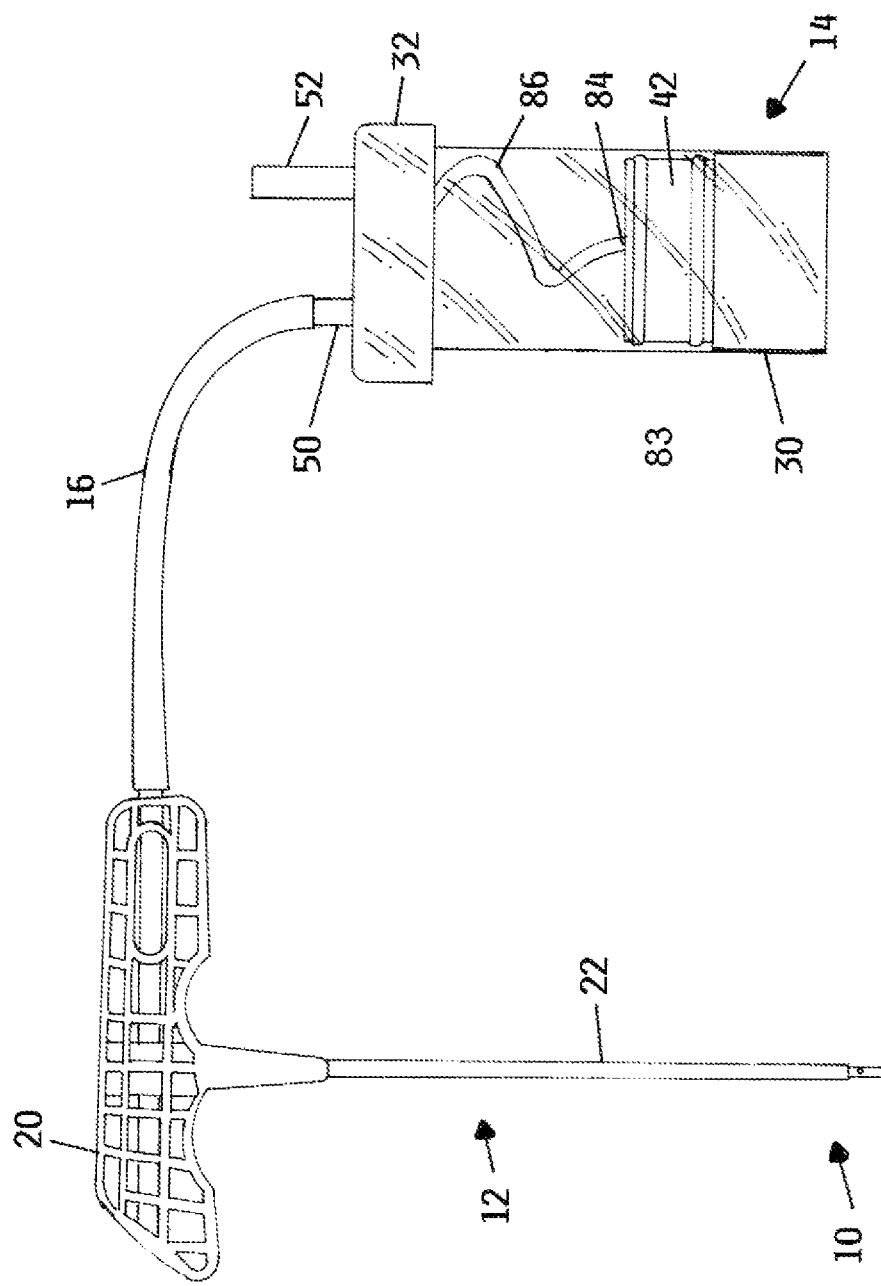
FIG. 3 is a side view of another embodiment of the bone fragment and tissue harvesting and processing system.

Another embodiment of the invention is directed to a bone fragment and tissue harvesting and processing system 10 that is used in conjunction with a harvesting device 12 by connection with tubing 14, which is illustrated in FIG. 3.

The bone fragment and tissue harvesting and processing system 10 receives bone fragments and tissue that are aspirated from a patient and then facilitates separation of desired components from the bone fragments and tissue prior to mixing the tissue with additional components such as a porous, biocompatible implantable matrix to form a bone void filler.

The invention thereby provides a completely autologous process that enables use of the patient's own tissue. The invention enables high yield harvesting of bone fragments, stem and progenitor cells in a process that is safe, fast and efficient. This bone fragments and tissue are used in conjunction with an osteoconductive matrix to form a bone graft.

The harvesting device 12 includes a handle portion 20 and a needle portion 22 that are operably connected to each other. In certain embodiments, the needle portion 22 is detachably connected to the handle portion 20.

The needle portion 22 includes a sharpened end that facilitates accessing the interior of a bone. Thereafter, the harvesting device 12 may be manipulated to form bone fragment and morselize the tissue. This enhances the amount of bone fragments and tissue that can be recovered from a patient. The bone fragments and tissue are aspirated from the patient using the harvesting device 12, which causes these components to be collected in the processing device 14.

The processing device 14 generally includes a collection vessel 30 to which a collection vessel cap 32 is operably attached. The collection vessel 30 may be formed with a size based upon the volume of bone fragments and tissue that are anticipated to be aspirated from the patient. In certain embodiments, the collection vessel 30 has a volume of about 180 cubic centimeters.

The collection vessel 30 may have a variety of shapes using the concepts of the invention. In certain embodiments, the collection vessel 30 has a generally cylindrical shape. Using such a shape enables the collection vessel cap 32 to be attached using a rotational motion. The cylindrical shape also facilitates the use of the processing piston 42 to be positioned in the collection vessel 30, as is described in more detail herein.

A side of the collection vessel 30 may include at least two volume collected markers. In one embodiment, the volume collected markers include an upper marker and a lower marker. The upper marker and the lower marker thereby provide guidance to the person using the invention regarding whether a desired volume of bone fragments and tissue have been collected. In other embodiments, the volume collected markers may include a series of identifiers that correspond to a conventional volume measuring system such as milliliters.

Proximate an upper end of the collection vessel 30, an opening 34 may be provided through which the aspirated bone fragment and tissue may be introduced into the collection vessel 30. In one such embodiment, the opening 34 is generally circular and has a thread on a surface thereof that can be used when attaching the collection vessel cap 32 to the collection vessel 30. In certain embodiments, the thread may be on an outer surface of the opening 34. A person of skill in the art will appreciate that a variety of other techniques may be used to attach the collection vessel cap 32 to the collection vessel 30.

One aspect of the attachment of the collection vessel cap 32 to the collection vessel 30 is that a substantially air-tight seal is formed when the collection vessel cap 32 is attached to the collection vessel 30 so that a vacuum may be used to draw the aspirated osteomedullary tissue into the collection vessel 30.

The collection vessel 30 may be fabricated from a variety of materials using the concepts of the invention. In one embodiment, at least a portion of the collection vessel 30 is fabricated from a transparent material. Such a configuration enables a person using the osteomedullary tissue collection and processing device 10 to not only view the volume of aspirated tissue in the collection vessel 30 but also other characteristics of the aspirated tissue such as a color of the aspirated tissue and/or the presence of discrete regions in the aspirated tissue.

Another criterion for the material that is used in fabricating the collection vessel 30 is that the material be biologically compatible and facilitate sterilization of the collection vessel 30 prior to use. An example of one such material that may be used to fabricate the collection vessel 30 is polyethylene terephthalate.

The collection vessel cap 32 includes a lower cap section 40. The lower cap section 40 may have a generally cylindrical configuration with an inner diameter that is selected based upon an outer diameter of the collection vessel 30 proximate the threaded region. The lower cap section 40 facilitates attachment of the collection vessel cap 32 to the collection vessel 30. In this regard, the collection vessel cap 32 may include a thread on an inner surface thereof that is shaped generally complementary to the thread on the collection vessel 30.

While not illustrated, at least a portion of the outer surface of the lower cap section 40 may have a shape and/or texture that enhances the ability to grasp the collection vessel cap 32 and turn the collection vessel cap 32 with respect to the collection vessel 30. Because of the nature of the invention and the potential desire to remove the collection vessel cap 32, the collection vessel cap 32 is typically intended to be tightened and loosened using manual force.

The collection vessel cap 32 includes a first port 50 and a second port 52 formed therein. A person of skill in the art will appreciate that at least one of the first port 50 and the second port 52 may alternatively be formed in the collection vessel 30.

The first port 50 includes a connector that facilitates attachment to another object such as tubing. In certain embodiments, the first port 50 enables tubing to be attached and detached. When the objects are attached, a substantially gas-impervious seal is formed. The first port 50 may include a standardized connector profile that enables a variety of objects to be attached thereto. An example of one suitable standardized connector is marketed under the identifier Leur Lock.

The second port 52 may be provided in a spaced-apart relationship from the first port 50 to minimize the potential of the aspirated osteomedullary tissue flowing directly from the second portion 52 to the first port 50 as opposed to being collected in the collection vessel 30. Similar to the first port 50, the second port 52 may be formed with a standardized connector profile. An example of one such connector profile that can be used for the second port 52 is a tapered push-on connector that facilitates a friction connection. In such embodiments, the push-on connector includes a plurality of ridges, which reduce the potential of the tubing or other object becoming detached from the second port 52.

The collection vessel cap 32 may be fabricated from a variety of materials using the concepts of the invention. In one embodiment, at least a portion of the collection vessel cap 32 is fabricated from a transparent material.

Another criterion for the material that is used in fabricating the collection vessel cap 32 is that the material be biologically compatible and facilitate sterilization of the collection vessel cap 32 prior to use. An example of one such material that may be used to fabricate the collection vessel cap 32 is polyethylene terephthalate.

To further reduce the potential of loss of the aspirated bone fragments and tissue that is collected in the processing device 14, a hydrophilic membrane valve (not shown) may be attached to the second port 52 intermediate the osteomedullary processing device 14 and the vacuum source. The hydrophilic membrane valve allows the vacuum to pull gas therethrough until the hydrophilic membrane becomes wet such as when the processing device 14 is knocked over or the processing device 14 is overfilled with liquid. The hydrophilic membrane valve thereby prevents the aspirated osteomedullary tissue from being drawn out of the processing device 14.

To minimize the potential of the processing device 14 being moved from a vertical orientation, the processing device 14 may be placed in a base 56 having a width that is greater than the width of the processing device 14. In certain embodiments, the base 56 has a width that is at least two times the width of the processing device 14. In one configuration, the base 56 includes a plurality of legs 58 extending therefrom. The legs may be positioned in a spaced-apart configuration around the based 56.

An alternative or additional technique to minimize the potential of aspirated bone fragments and tissue being drawn into the vacuum line may include attaching the processing device 14 to an object proximate to the patient from which the bone fragments and tissue are being aspirated. An example of one suitable option is a clip that attaches the processing device 14 to an IV pole, a drape near the patient or the operating table.

In certain embodiments, an attachment device (not shown) may include a first portion and a second portion. The first portion extends around at least a portion of the collection vessel 30 to engage the collection vessel 30. In certain embodiments, the first portion may include an opening that receives the collection vessel 30. In another embodiment, the first portion extends substantially around the collection vessel 30 proximate to where the collection vessel cap 32 attaches to the collection vessel 30. The second portion includes a clip or similar device that enables the attachment device to be attached to an object in the operating room such as a drape.

The processing piston 42 is intended for slidable movement with respect to the collection vessel 30. The processing piston 42 thereby substantially encloses an upper end of the collection vessel 30 while facilitating changing of the volume enclosed therein.

The processing piston 42 thereby has a shape that generally conforms to the shape of the collection vessel 30 but is formed with a diameter that is slightly smaller than the inner diameters of the collection vessel 30.

The processing piston 42 is fabricated from a material that is less dense than the tissue fluid such that as the fluid is collected in the collection vessel 30 increases, the processing piston 42 raises in the collection vessel 30. In one such embodiment, the processing piston 42 is substantially hollow.

The processing piston 42 has a height and a width that restrict the processing piston 42 to only moving in a generally vertical direction between an upper end and a lower end of the collection vessel 30. In one such embodiment, a height of the processing piston 42 is at least about ⅓ of an inner diameter of the collection vessel 30.

As is described in more detail below, a vacuum is used to cause the bone fragments and tissue to be withdrawn from the patient. Because there is no seal between the processing piston 42 and the collection vessel 30, the vacuum does not affect the position of the processing piston 42 in the collection vessel 30. Rather, the vacuum has a substantially equal force throughout the interior of the collection vessel 30.

The processing piston 42 has a connection port 84 extending therefrom proximate an upper end thereof. The connection port 84 facilitates attachment of tubing 86 to the processing piston 42. The processing piston 42 also includes a bore 83 that extends from the connection port 84 to a lower surface of the processing piston 42. The configuration of the processing piston 42 thereby facilitates material in the collection vessel 30 to be withdrawn through the tubing 86. This process causes the material in the collection vessel 30 that is proximate the processing piston 42 to be withdrawn through the tubing 86. As the material is withdrawn from the collection vessel 30, the processing piston 42 moves with respect to the collection vessel 30.

Figure 11:
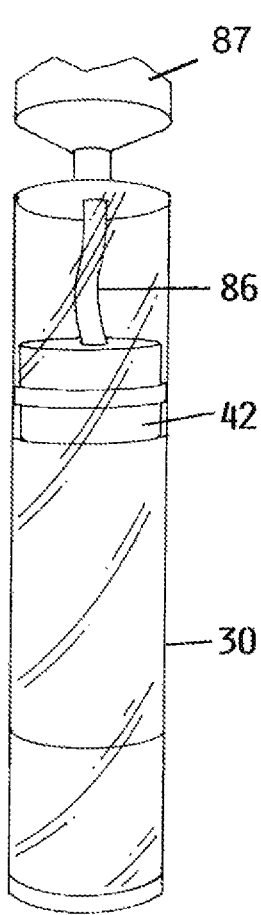
FIG. 11 is a first position of the processing piston in the osteomedullary tissue collection and processing device of FIG. 9.
Figure 12:
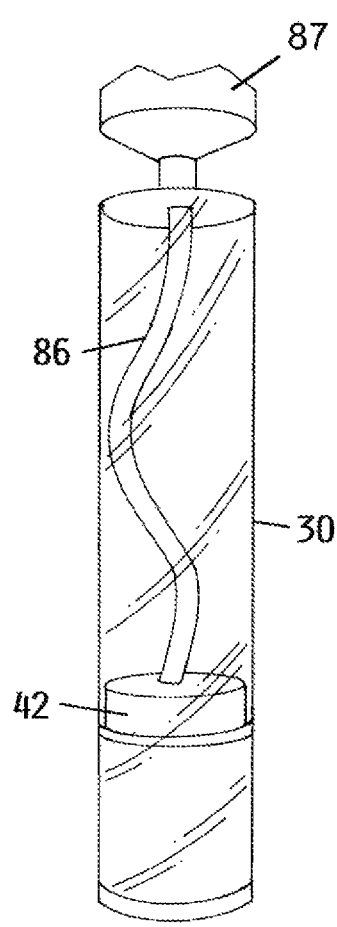
FIG. 12 is a second position of the processing piston in the osteomedullary tissue collection and processing device of FIG. 9.
Figure 13:
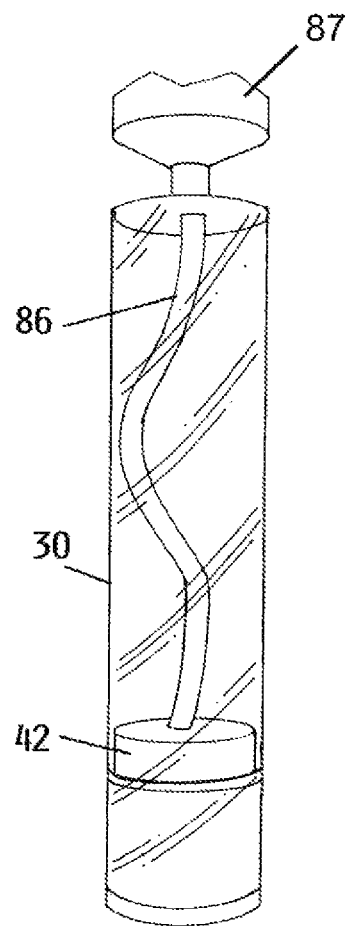
FIG. 13 is a third position of the processing piston in the osteomedullary tissue collection and processing device of FIG. 9.

An end of the tubing 86 opposite the processing piston 42 engages the first port 50 on a lower surface of the collection vessel cap 32 so that fluid that is harvested from the patient flows through tubing 16, then through the tubing 86 and is deposited in the collection vessel 30. In another embodiment, the collection vessel cap 32 is detached from the collection vessel 30 as illustrated in FIGS. 11-13. The tubing 86 is connected to a fluid withdrawal mechanism such as a syringe 87 such as is described in more detail below with respect to FIGS. 11-13.

The tubing 86 may have a relatively small inner diameter such as between about 1 and about 5 millimeters. At least a portion of the tubing 86 may be fabricated from a transparent material to evaluate the characteristics of the material being withdrawn through the tubing 86. This combination of the tubing small inner diameter and the transparent nature facilitates separation of the beneficial components in the withdrawn tissue from the red blood cells, which will remain in the collection vessel 30 using the process, which is described in more detail herein.

Prior to use, the components of the processing device 14 may be sterilized. A person of skill in the art will appreciate that a variety of sterilization techniques may be used. An example of one suitable sterilization technique is exposure of the packaged components to gamma radiation.

As an initial step in harvesting the bone fragments and tissue, the collection vessel cap 32 is attached to the collection vessel 30 so that the processing device 14 looks substantially as illustrated in FIG. 3. The osteomedullary tissue harvesting device 12 is attached to the processing device 14 using the tubing 14. A vacuum source is attached to the second port 52.

A site is selected from which the bone fragments and tissue are to be harvested. It is possible to use the invention in conjunction with harvesting bone fragments and tissue from a variety of bones in a patient. Preferred sites for harvesting the bone fragments and tissue include the iliac crest and pedicle/vertebral bodies.

A guide wire (not shown) may be used to identify a location at which the needle portion 22 is to be extended into the bone. An imaging technique such as a fluoroscope may be used to assist in the placement and orientation of the guide wire.

The needle portion 22 is extended over the guide wire and into the bone to access the area where the osteomedullary tissue is located. To enhance the volume of bone fragments and tissue that can be aspirated, the needle portion 22 may be pivoted so that the distal end of the needle portion 22 moves through the interior of the bone to cause bone fragments to be formed and cause morselizing of the tissue. This process significantly increases the volume of beneficial bone fragments and tissue that can be harvested as compared to conventional processing techniques that merely insert the aspiration needle into the bone at different depths.

A vacuum is applied to the system. The person using the system may control application of the vacuum to the needle portion 22 by placing his/her finger over a valve opening 60. When the valve opening 60 is substantially covered, the vacuum is drawn through the needle portion 22 to cause the bone fragments and tissue to be aspirated through the needle portion 22.

The aspirated bone fragments and tissue flow through the tubing 14 and into the processing device 14, where the aspirated bone fragments and tissue accumulates in the collection vessel 30. This process is continued until a desired volume of bone fragments and tissue have been aspirated from the patient.

If it is not possible to obtain a desired volume of the bone fragments and tissue from a particular location, it may be necessary to insert the needle portion 22 into a different location in the bone. It may also be necessary to insert the needle portion 22 into a different bone.

It may be desirable to control the intensity of the vacuum that is pulled through the harvesting device 12. An example of one mechanism to control the vacuum level is using a valve that is operably attached to the vacuum line that is attached to the first port 50.

During the process of collecting the aspirated bone fragments and tissue in the processing device 14, it may be desirable to utilize a filter to separate the bone fragments from the other components in the aspirate so that the bone fragments can be utilized in forming the bone graft. A person of skill in the art will appreciate that a variety of techniques may be used to separate the bone fragments from the remainder of the aspirate.

Prior to forming bone graft using the aspirated tissue, it may be desirable for the red blood cells to be separated from the other components in the aspirated tissue. One technique that may be used to separate the red blood cells from the other portions of the aspirated tissue is by agglomerating the red blood cells.

Once the red blood cells are agglomerated, they become denser than the other materials in the aspirated tissue and thereby settle in the collection vessel. An advantage of using the red blood cell agglomerating technique is that it possible to separate a large portion of the red blood cells while minimizing the potential of damage to the other components in the aspirated osteomedullary tissue.

The red blood cells may be caused to agglomerate using a positively charged material. This positively charged material should be relatively inert with respect to the other desirable components in the aspirated osteomedullary tissue such that the positively charged material does not impact the beneficial properties of the aspirated tissue. Furthermore, the positively charged material should have no negative interactions if any of the positively charged material remains in the aspirated tissue, which then becomes incorporated into the bone graft and thereafter is implanted into the patient.

Figure 4:
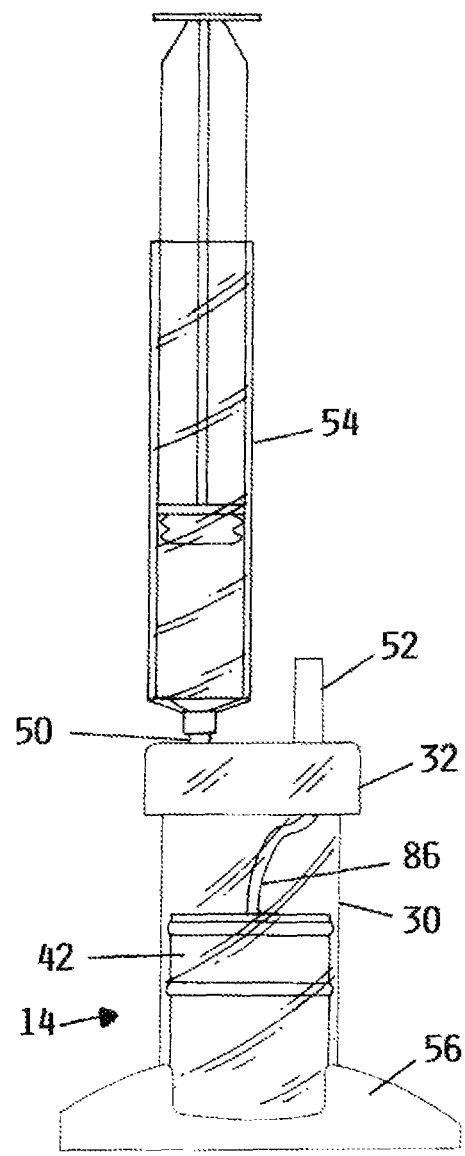
FIG. 4 is a side view of the bone fragment and tissue harvesting and processing system attached to a syringe for injecting red blood cell agglomerating material.

The red blood cell agglomerating material is added to the collection vessel 30 using a syringe 54, as illustrated in FIG. 4. A connection mechanism such as a Leur lock may be used to attach the syringe to the collection vessel 30.

In certain embodiments, the red blood cell agglomerating material is Prepacyte. The red blood cell agglomerating material is added at a volume so that substantially all of the red blood cells in the aspirated tissue are caused to agglomerate.

The volume of the red blood cell agglomerating material that is added to the collection vessel 30 is selected based upon the maximum amount of aspirated tissue that is intended to be collected in the collection vessel 30, as it is believed that an excess amount of the red blood cell agglomerating material does not negatively impact the properties of the aspirated tissue.

The time period for substantially all of the red blood cells in the collection vessel 30 to agglomerate may depend on a variety of factors. In certain embodiments, substantially all of the red blood cells agglomerate in less than about 10 minutes after the addition of the red blood cell agglomerating material to the collection vessel 30.

Figure 5:
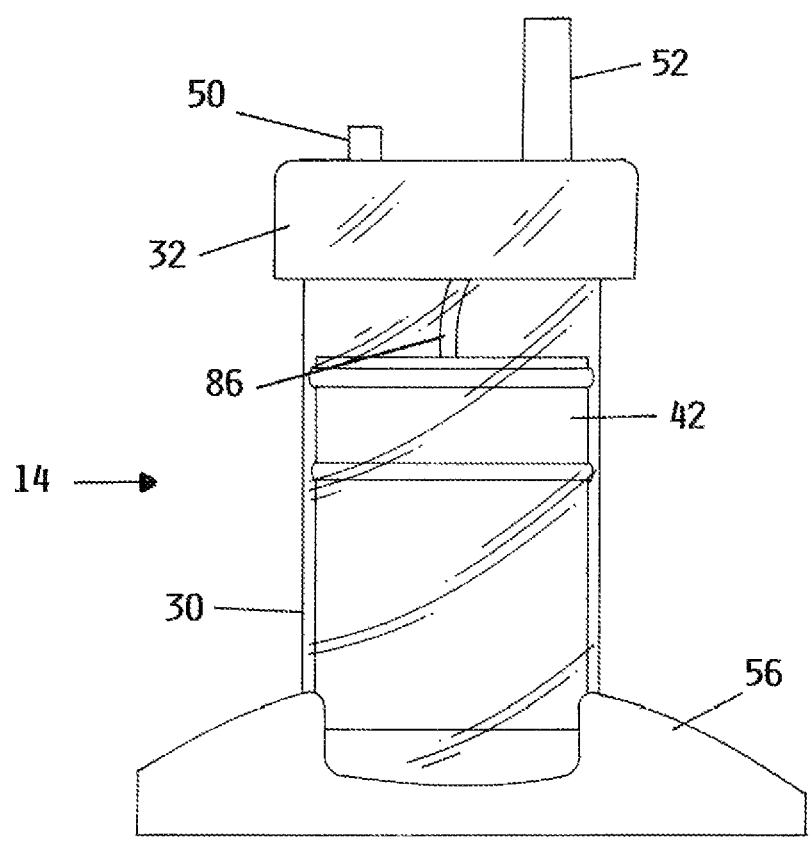
FIG. 5 is a side view of the bone fragment and tissue harvesting and processing system where agglomerated red blood cells have settled.

It may be possible to slowly agitate the collection vessel 30 to enhance the dispersal of the red blood cell agglomerating material throughout the aspirated tissue and thereby enhance the rate of the agglomerating process. Once the red blood cells have substantially all agglomerated, the agglomerated red blood cells are allowed to settle in the collection vessel 30, as illustrated in FIG. 5. The settled agglomerated red blood cells form a relatively well defined region proximate the bottom of the collection vessel 30.

Figure 6:
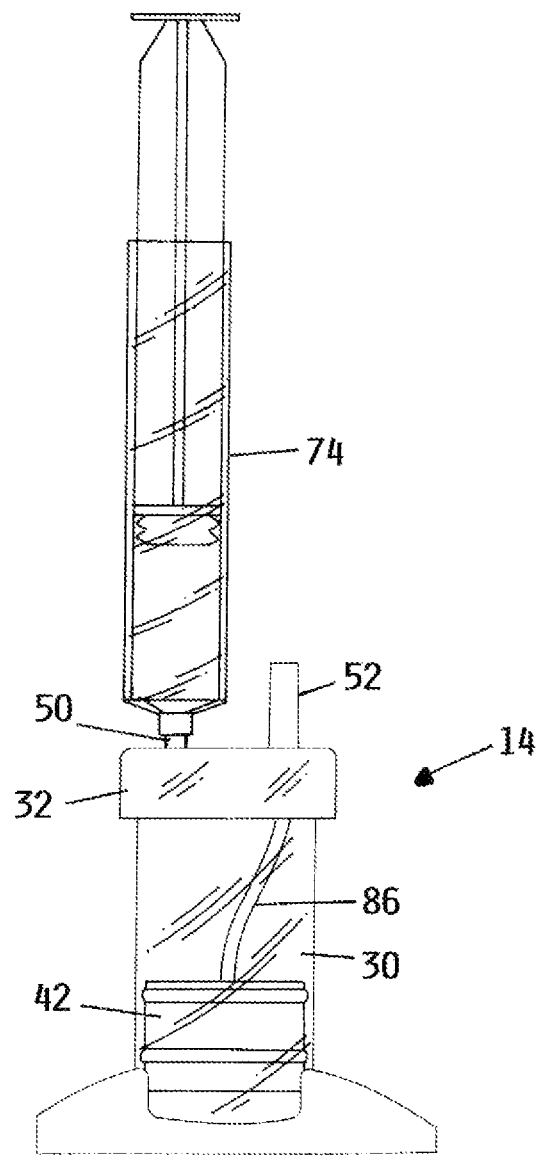
FIG. 6 is a side view of the bone fragment and tissue harvesting and processing system with a syringe attached hereto for removing the osteomedullary tissue other than the settled agglomerated red blood cells.

A syringe 74 is attached to the inlet port 50 of the collection vessel 30. The syringe 74 is used to withdraw the upper portion of the aspirated tissue that is above the settled agglomerated red blood cells, as illustrated in FIG. 6. As this fluid is withdrawn from the collection vessel 30, the processing piston 42 lowers in the collection vessel 30.

It is desired for substantially all of the fluid containing the aspirated tissue to be withdrawn from the collection vessel 30. The relatively narrow inner diameter and the clear material of the tubing 86 enables the person to continue withdrawing the fluid containing the aspirated tissue until a change of color of the fluid in the tubing 86 is identified as that color change indicates that the red blood cells are being drawn into the tubing 86.

Figures 7, 8:
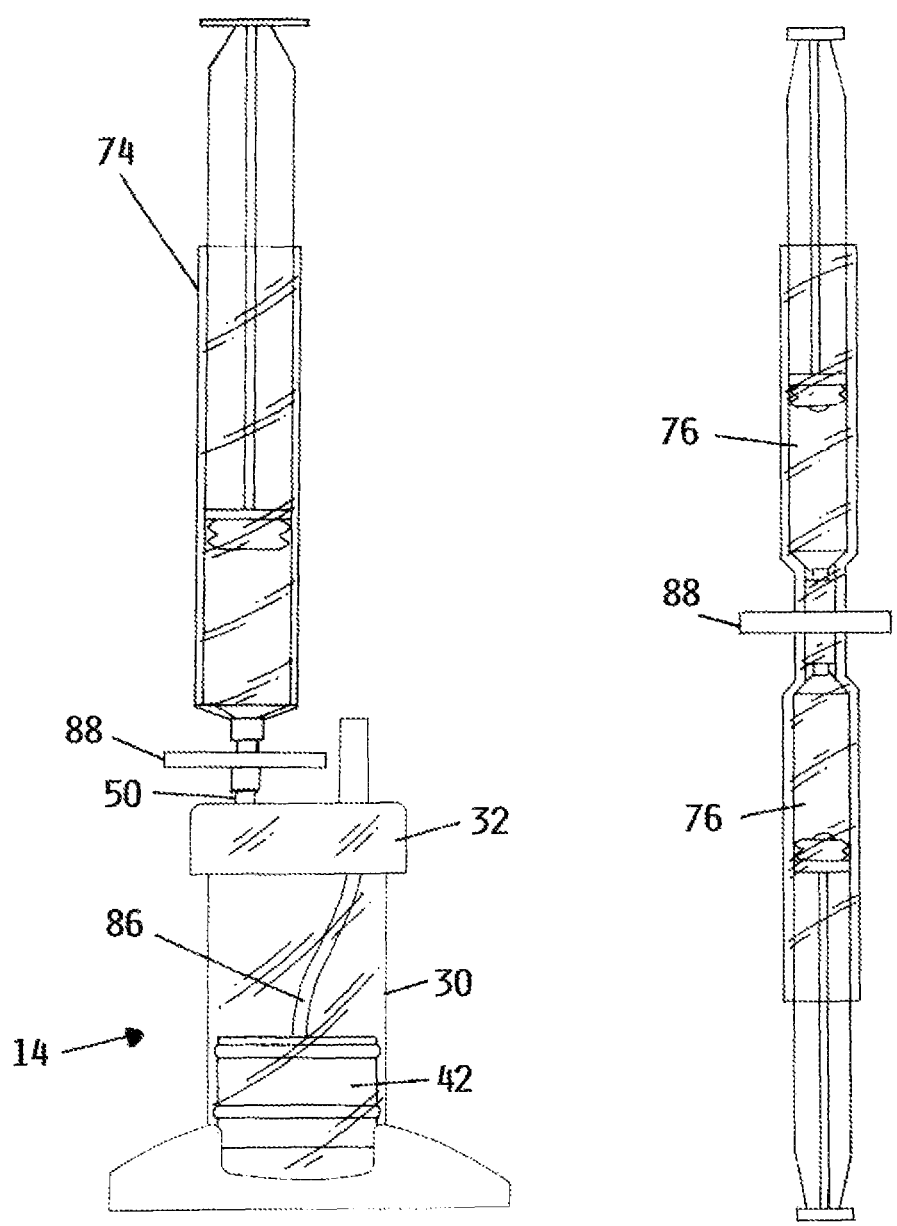
FIG. 7 is a side view of the bone fragment and tissue harvesting and processing system with a cell collection filter attached intermediate the syringe.
FIG. 8 is a side view of the cell collection filter positioned between two syringes for separating osteomedullary cells from the cell collection filter.

The syringe 74 is disconnected from the inlet port 50 and a cell collection filter 88 is attached between the syringe 74 and the collection vessel 30, as illustrated in FIG. 7. The cell collection filter 88 has a pore size that is sufficiently small so that substantially all of the progenitor cells and other beneficial tissue in the osteomedullary tissue are retained on the cell collection filter 88. The pore size of the cell collection filter 88 is sufficiently large so that there is not significant resistance to the liquid in the aspirated tissue passing through the cell collection filter 88.

The syringe 74 is depressed to cause the fluid containing the aspirated tissue to pass through the cell collection filter 88. The filter membrane in the cell collection filter 88 causes substantially all of the aspirated tissue to be retained thereon to separate the aspirated tissue from the remainder of the fluid.

The cell collection filter 88 is detached from the collection vessel 30 and a syringe 76 containing a rinsing fluid such as saline is attached to the cell collection filter 88, as illustrated in FIG. 8. The rinsing fluid causes the aspirated tissue to the washed from the cell collection filter 88.

Thereafter, the aspirated tissue is associated with a bone graft matrix. If bone fragments were collected as discussed above, the bone fragments may be utilized in preparing the bone graft matrix. A person of skill in the art will appreciate that a variety of bone graft matrices may be used. The bone graft matrix should be a cell binding and cell friendly, osteoconductive material. The osteoconductive matrix can be allogeneic, synthetic or a combination thereof. The allogeneic material can be provided in a variety of forms. Examples of two such suitable forms are granules and fibers.

The osteoconductive matrix may include at least one of demineralized bone matrix, a suitable synthetic alternative such as hydroxyapatite with the addition of other materials that fall within the classification of extracellular matrix. Examples of these materials include hyaluronic acid, collagen, keratin, elastin, fibronectin and laminin.

The allograft can be provided as mineralized or demineralized depending on the intended use of the graft. In certain embodiments, the allograft granules have a particle size that is between about 3 millimeters and about 100 microns.

Examples of the synthetic materials include calcium phosphate, tri-calcium phosphate, hydroxyapatite or combinations thereof. The synthetic materials may be provided in a variety of particle sizes such as between about 3,000 microns and 60 microns.

The osteoconductive matrix can be configured as a filter for selective retention of the desirable constituents of red blood cell depleted osteomedullary tissue whereby the osteoconductive matrix filters the desirable constituents by means of mechanical filtering such as by controlled porosity and/or by means of selective surface binding such as affinity chromatography like effect.

In certain embodiments, the combination includes greater than about 50% by weight demineralized bone matrix or synthetic substitute thereof. In other embodiments, the combination includes demineralized bone matrix or synthetic substitute thereof at a concentration of between about 60% and 90% by weight.

The osteoconductive matrix that is used in preparing the bone graft may be provided in a variety of forms such as powder, small particles or in the shape of the implant. The osteoconductive matrix can be obtained from various commercial sources such as AlloSource, Cryolife or RTI Biologics.

In certain embodiments, the osteoconductive matrix may have an average particle size of less than about 1 millimeter. In other embodiments, the osteoconductive matrix may have an average particle size of less than about 0.5 millimeters.

Because of the intended in-vivo use of the bone graft, the osteoconductive matrix should be provided in a sterile configuration to minimize the potential of introducing pathogens during the process of implanting the bone graft. Prior to using the bone graft, the components used to fabricate the bone graft should be relatively uniformly mixed.

The osteoconductive matrix may be compacted when being placed in the cartridge 170 to enhance the uniformity at which the aspirated osteomedullary tissue will pass through the osteoconductive matrix.

In addition to using a chromatography effect to selectively retain the efficacious components in the red blood cell depleted aspirated tissue in the filtering osteoconductive matrix, e.g., a demineralized bone plus extracellular matrix composite, it is also possible to use a mechanical entrapment or filtering effect to selectively retain the efficacious components in the aspirate osteomedullary tissue in the osteoconductive matrix.

The osteoconductive matrix may have a multi-strata configuration. In certain embodiments, the osteoconductive matrix is configured to go from high inherent porosity proximate the inlet to lower inherent porosity proximate the outlet. Alternatively, it may be possible to use a reverse descending strata configuration to help keep the smallest particles in place.

For example, a more coarsely ground osteoconductive matrix may be placed proximate the entry port of the cartridge and more finely ground osteoconductive matrix may be placed proximate the outlet port of the cartridge. It is also possible to put one or more additional layers between the more coarsely ground layer and the more finely ground layer that progressively include more finely ground particles.

The osteoconductive matrix may consist of a thin layer of 250+ micron particles that is placed on the membrane. Next, a slightly thicker layer of 100+ micron particles is placed in the cartridge. This process is repeated with 250+ micron particles, 500+ micron particles, 1,000+ micron particles and 3,000+ micron particles.

The effective porosity of a bed of granules is between about 25 percent and about 30 percent of the granule size. For example, a bed of 100 micron granules will exhibit an effective porosity of about 25 microns to about 30 microns. The typical granule size range of sieved particles can be less than 40 microns, between 60 microns and 100 microns, between 100 microns and 250 microns, between 250 microns and 500 microns, between 500 microns and 1,000 microns, between 1,000 microns and 3,000 microns and greater than 3,000 microns.

The aspirated osteomedullary tissue will be introduced at the top of the cartridge 70 and then pass through the 3,000 micron layer and then the 1,000 micron layer and so on. The larger constituents that may be in the aspirated osteomedullary tissue such as small pieces of bone, cartilage or thrombus will be trapped in the first layer but the smaller constituents will pass through all the way down to the stem cell size, which will be trapped in the 60 micron layer or the 100 micron layers as the size of these cells is in the range of 15 to 50 microns.

One beneficial technique for associating the osteomedullary tissue with the bone graft matrix is using a syringe. A benefit of using the syringe to cause the suction to be drawn on the second end of the bone graft mixing container is that a sufficient vacuum is applied to cause the osteomedullary tissue to be drawn through the matrix in the bone graft matrix without the force being too large such that the osteomedullary tissue is caused to form a channel through the bone graft matrix. The force is continued into a desired volume of the osteomedullary tissue is drawn through the bone graft matrix. A benefit of this process is that the osteomedullary tissue cells are substantially unaffected and undamaged during the process of forming the bone graft matrix.

It is also possible to utilize an affinity mechanism to trap desirable cells in the bone matrix. This process may be a preferred retention mechanism as in certain configurations, it is more discriminating for the preferred cells rather than just size. A person of skill in the art will appreciate that a variety of compositions may be utilized based upon the cells that are desired to be trapped in the bone matrix. For example, the attractant composition may exhibit a charge that causes the desired cells to be attracted to the bone matrix.

Red blood cells have a particle size of about 7 micrometers. White blood cells have a particle size of between about 15 and 18 micrometers. The beneficial osteomedullary and progenitor cells in the bone marrow aspirate have a particle size of between about 35 and 50 micrometers.

As a result of this situation is that the osteomedullary cells have a size that is considerably larger than the other components in the bone marrow aspirate, this size difference can be used to facilitate retention of the osteomedullary cells in the filter container while the much smaller red blood cells and white blood cells pass through the filter container.

In addition to utilizing the affinity of the osteomedullary tissue to the bone fragments and the size of the osteomedullary tissue to facilitate separation, it is also possible to process the material that collections in the collection vessel 30 to separate the red blood cells therefrom and then use the red blood cell depleted tissue in forming the bone graft. The process and device described herein thereby facilitates recovering substantially all of the beneficial cells from the tissue that is aspirated from the patient.

The system described herein thereby results in the aspiration of a significant amount of bone matrix. This system also results in multiple mechanisms for recovering beneficial cells from within the bone. The first mechanism encompasses the beneficial cells that are associated with the bone fragments. The second mechanism relates to the selective retention of the beneficial cells as the aspirate is passed through the filter container. The third mechanism is from the material that collects in the collection vessel and from which the red blood cells are separated as described in more detail herein.

The combined result of using these three mechanisms enables substantially all of the beneficial cells in the aspirated tissue is recovered. Such recovery represents a significant enhancement when compared to the prior techniques, which in addition to utilizing an inefficient harvesting process, recovered a much smaller percentage of the beneficial cells from the harvested tissue.

Depending on the desired application of the bone paste, the bone paste can be formed with different flowabilities. The flowability of the bone paste can be adjusted by changing the amount of water in the bone marrow aspirate concentrate as well as the amount of water that is allowed to pass through the filter membrane at the second end of the cartridge.

Alternatively, to applying the bone graft as a paste, it is possible to form the bone graft material into the desired shape of the implant. After the bone graft material is formed into the desired shape, the moisture content of the bone graft material can be reduced to cause the implant to become more rigid. An example of one technique that may be used to reduce the moisture content of the implant is heating.

The physical properties of the bone graft material may be enhanced by the addition of at least one additive to the bone graft material. An example of one additive is collagen.

The total time from harvesting of the cells from the patient to having a bone graft that is ready for use in the patient can be done in a relatively short period of time. In certain embodiments, the process takes less than one hour. In other embodiments, the process takes between about 30 minutes and about 40 minutes.

Another advantage of the osteomedullary tissue process system described herein is that it is a closed system. Such a closed system facilitates use of the osteomedullary tissue processing system in non-sterile environments such as a doctor's office, as compared to a sterile environment that is typically only found in an operating room.

The beneficial portions of the osteomedullary tissue (progenitor cells) can be retained in a relatively small volume of a bone graft material such as tricalcium phosphate. In certain embodiments, the bone graft material is selected with an effective porosity of between about 20 and 30 percent.

Using such a process, it is possible to prepare a bone graft base that contains the osteomedullary tissue where the level of bone graft material is relatively small compared to the volume of osteomedullary tissue. Proximate the when it is desired to use the bone graft material, the bone graft base is mixed with a primary bone graft material.

In this configuration, the concentration of the primary bone graft material may be greater than the concentration of the base bone graft material. Using such a configuration, a surgeon is able to obtain the benefits associated with using a bone graft that contains osteomedullary tissue while at the same time being able to use a primary bone graft material that the surgeon prefers.

The bone graft base may be fabricated with a relatively low viscosity such that when the bone graft base is mixed with the primary bone graft material, the bone graft thereby produced has a desired viscosity.

The concentration of the bone graft base in the bone graft may be between about 10 percent and about 90 percent. In other embodiments, the concentration of the bone graft base in the bone graft is between about 20 percent and about 50 percent.

The invention results in a purified cell solution that can be used in a number of applications such as bone graft enrichment and stem cell enriched injectable. The concentrated bone marrow cells can also be used in conjunction with a variety of other applications. Examples of these applications include repair of strained or torn ligaments or tendons and restoring early osteoarthritis cartilage loss as well as treating radiculopathy. Such treatments can slow the progression of certain diseases and thereby delay or eliminate the need for surgery. Through the use of the invention, patients are able to significantly improve their overall quality of life.

Another aspect of the invention is directed to using the invention to provide stem cell injections such as to treat soft tissue injuries such as tendons, ligaments and cartilage. When the invention is used in conjunction with stem cell injections, the cells can be concentrated from the purified solution. Thereafter, the cells can be re-suspended in an injectable carrier. Similar to the use of the invention in conjunction with bone grafts, this embodiment can be completed in a relatively short period of time such as less than one hour. In other embodiments, the time to prepare the injectable stem cells is between about 30 minutes and about 40 minutes.

At least a portion of the components of the osteomedullary tissue harvesting system may be disposable such that after a single use of the items, the items are discarded. In other embodiments, at least a portion of the components of the osteomedullary tissue harvesting system may be configured to be cleanable and sterilizable such that the components can be reused in subsequent surgical procedures.

Figure 9:
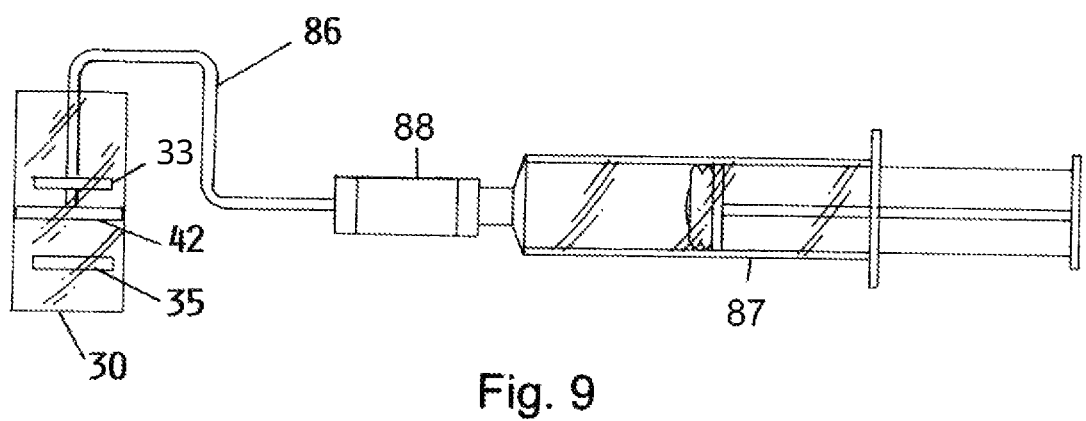
FIG. 9 is a side view of an alternative embodiment of the osteomedullary tissue collection and processing device attached to a bone graft mixing container and a syringe.

Another embodiment of the invention includes a collection vessel 30 in which a processing piston 42 is slidably, as illustrated in FIG. 9. The processing piston 42 thereby substantially encloses an upper end of the collection vessel 30 while facilitating changing of the volume enclosed therein.

The processing piston 42 thereby has a shape that generally conforms to the shape of the collection vessel 30 but is formed with a diameter that is slightly smaller than the inner diameters of the collection vessel 30.

Figure 10:
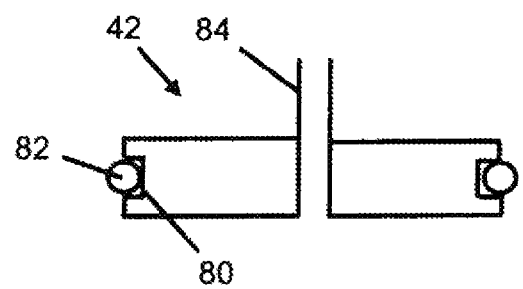
FIG. 10 is a sectional view of a processing piston for use in conjunction with the osteomedullary tissue collection and processing device of FIG. 9.

An outer edge of the processing piston 42 has a channel 80 formed therein that is adapted to receive a sealing material such as an O-ring 82, as illustrated in FIG. 10. When the processing piston 42 is placed in the collection vessel 30, the O-ring 82 substantially seals with the inner surface of the collection vessel 30.

The processing piston 42 has a connection port 84 extending therefrom. The connection port 84 facilitates attachment of tubing 86 to the processing piston 42. The configuration of the processing piston 42 thereby facilitates material in the collection vessel 30 to be withdrawn through the tubing 86. This process causes the material in the collection vessel 30 that is proximate the processing piston 42 to be withdrawn through the tubing 86. As the material is withdrawn from the collection vessel 30, the processing piston 42 moves with respect to the collection vessel 30.

The tubing 86 may have a relatively small inner diameter such as between about 1 and about 5 millimeters. At least a portion of the tubing 86 may be fabricated from a transparent material to evaluate the characteristics of the material being withdrawn through the tubing 86. This combination of the tubing small inner diameter and the transparent nature facilitates separation of the beneficial components in the withdrawn osteomedullary tissue from the red blood cells, which will remain in the collection vessel 30 using the process, which is described in more detail herein.

As an initial step in recovering the beneficial components from the aspirated tissue, it may be desirable for the red blood cells to be separated from the other components in the aspirated tissue. One technique that may be used to separate the red blood cells from the other portions of the aspirated tissue is by agglomerating the red blood cells. Once the red blood cells are agglomerated, they become denser than the other materials in the aspirated tissue and thereby settle in the collection vessel. An advantage of using the red blood cell agglomerating technique is that it possible to separate a large portion of the red blood cells while minimizing the potential of damage to the other components in the aspirated tissue.

The red blood cells may be caused to agglomerate using a positively charged material. This positively charged material should be relatively inert with respect to the other desirable components in the aspirated osteomedullary tissue such that the positively charged material does not impact the beneficial properties of the aspirated osteomedullary tissue. Furthermore, the positively charged material should have no negative interactions if any of the positively charged material remains in the aspirated osteomedullary tissue, which then becomes incorporated into the bone graft and thereafter is implanted into the patient.

In certain embodiments, the red blood cell agglomerating material is Prepacyte. The red blood cell agglomerating material is added at a volume so that substantially all of the red blood cells in the aspirated osteomedullary tissue are caused to agglomerate.

The red blood cell agglomerating material is added to the collection vessel 30 such as using a syringe. The volume of the red blood cell agglomerating material that is added to the collection vessel 30 is selected based upon the maximum amount of osteomedullary tissue that is to be collected in the collection vessel 30, as it is believed that an excess amount of the red blood cell agglomerating material does not negatively impact the properties of the osteomedullary tissue.

The time period for substantially all of the red blood cells in the collection vessel 30 to agglomerate may depend on a variety of factors. In certain embodiments, substantially all of the red blood cells agglomerate in less than about 10 minutes after the addition of the red blood cell agglomerating material to the collection vessel 30.

It may be possible to slowly agitate the collection vessel 30 to enhance the dispersal of the red blood cell agglomerating material throughout the aspirated osteomedullary tissue and thereby enhance the rate of the agglomerating process. Once the red blood cells have substantially all agglomerated, the agglomerated red blood cells are allowed to settle in the collection vessel 30, as illustrated in FIG. 11.

The syringe is used to withdraw the material other than the agglomerated and settled red blood cells from the collection vessel 30. As this material is withdrawn, the processing piston 42 lowers in the collection vessel 30, as illustrated in FIG. 12. The withdrawing is continued until the color of the fluid in the tubing 86 changes from relatively clear to a red color, as illustrated in FIG. 13. This change of color is indicative of the agglomerated red blood cells being drawn into the tubing. The syringe is detached and the fluid therein is available for further processing such as in preparing the bone graft.

Figure 14:
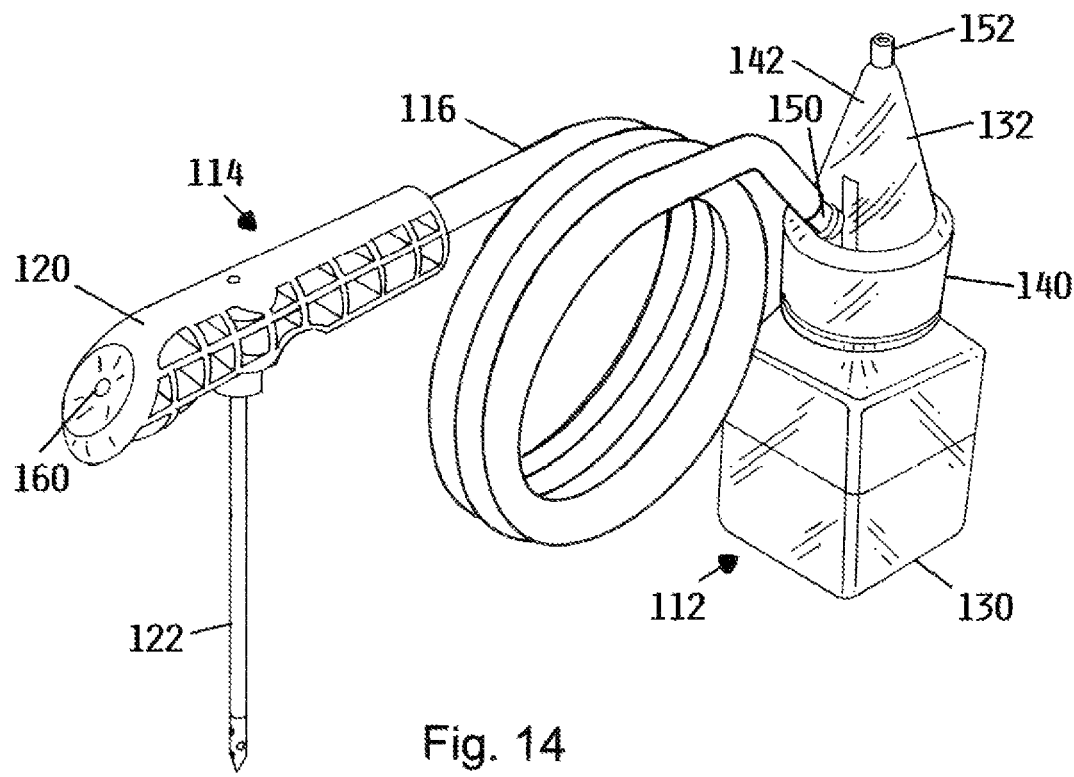
FIG. 14 is a perspective view of an osteomedullary tissue collection and processing device according to an alternative embodiment of the invention that is used in conjunction with the osteomedullary tissue harvesting device.
Figure 15:
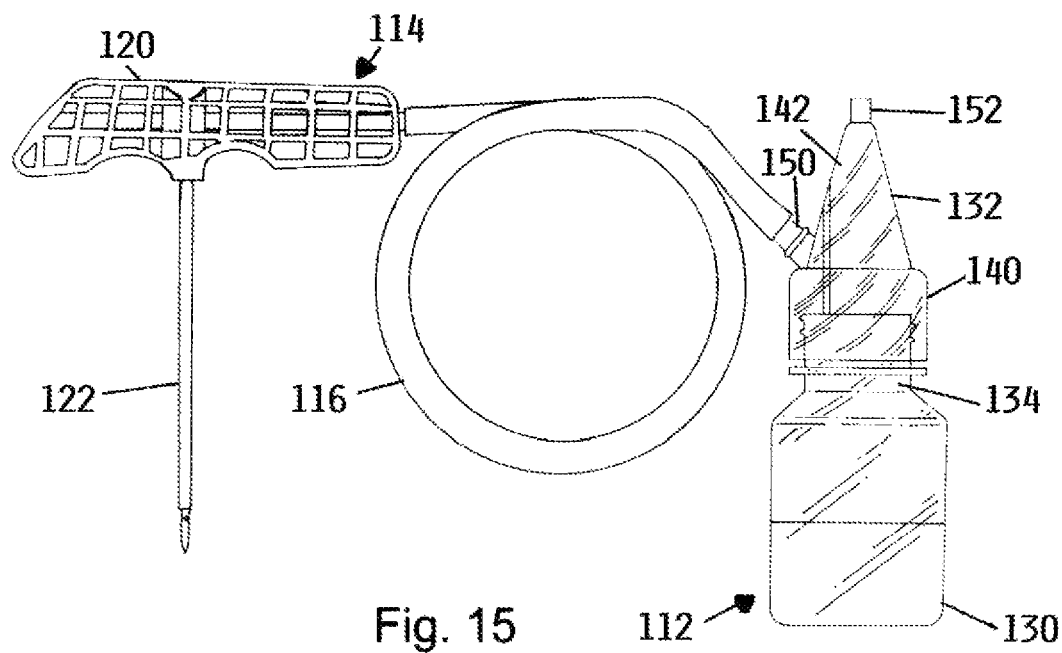
FIG. 15 is a side view of the osteomedullary tissue collection and processing device of FIG. 14 attached to the osteomedullary tissue harvesting device.

Another embodiment of the invention is directed to a bone fragment and tissue collection and processing device 112 that is used in conjunction with a bone fragment and osteomedullary tissue harvesting device 114 by connection with tubing 116, which is illustrated in FIGS. 14 and 15.

The bone fragment and tissue collection and processing device 112 generally includes a collection vessel 130 to which a collection vessel cap 132 is operably attached. The collection vessel 130 may be formed with a size based upon the volume of bone fragments and osteomedullary tissue that is anticipated to be aspirated from the patient. In certain embodiments, the collection vessel 130 has a volume of about 125 milliliters.

The collection vessel 130 may be formed with a shape that reduces the potential of the collection vessel 130 being inadvertently knocked over. In one such configuration, a lower surface of the collection vessel 130 may be substantially flat. In this embodiment, the collection vessel 130 may have a generally square or rectangular profile as illustrated in the figures.

Proximate an upper end of the collection vessel 130, an opening 134 may be provided through which the aspirated tissue may be introduced into the collection vessel 130. In one such embodiment, the opening 134 is generally circular and has a thread on a surface thereof that can be used when attaching the collection vessel cap 132 to the collection vessel 130. In certain embodiments, the thread may be on an outer surface of the opening 134. A person of skill in the art will appreciate that a variety of other techniques may be used to attach the collection vessel cap 132 to the collection vessel 130. In certain embodiments, the collection vessel cap 132 may be permanently attached to the collection vessel 130.

One aspect of the attachment of the collection vessel cap 132 to the collection vessel 130 is that a substantially air-tight seal is formed when the collection vessel cap 132 is attached to the collection vessel 130 so that a vacuum may be used to draw the aspirated osteomedullary tissue into the collection vessel 130.

The collection vessel 130 may be fabricated from a variety of materials using the concepts of the invention. In one embodiment, at least a portion of the collection vessel 130 is fabricated from a transparent material. Such a configuration enables a person using the osteomedullary tissue collection and processing device 112 to not only view the volume of aspirated tissue in the collection vessel 130 but also other characteristics of the aspirated tissue such as a color of the aspirated tissue and/or the presence of discrete regions in the aspirated tissue.

Another criterion for the material that is used in fabricating the collection vessel 130 is that the material be biologically compatible and facilitate sterilization of the collection vessel 130 prior to use. An example of one such material that may be used to fabricate the collection vessel 130 is polyethylene terephthalate.

The collection vessel cap 132 includes a lower cap section 40 and an upper cap section 142. The lower cap section 140 may have a generally cylindrical configuration with an inner diameter that is selected based upon an outer diameter of the collection vessel 130 proximate the threaded region. The lower cap section 140 facilitates attachment of the collection vessel cap 132 to the collection vessel 130. In this regard, the collection vessel cap 132 may include a thread on an inner surface thereof that is shaped generally complementary to the thread on the collection vessel 130.

While not illustrated at least a portion of the outer surface of the lower cap section 140 may have a shape and/or texture that enhances the ability to grasp the collection vessel cap 132 and turn the collection vessel cap 132 with respect to the collection vessel 130. Because of the nature of the invention and the potential desire to remove the collection vessel cap 132, the collection vessel cap 132 is typically intended to be tightened and loosened using manual force.

The upper cap section 142 may have a generally tapered shape as illustrated in the figures. The tapered shape enhances the ability to separate precipitated red blood cells from the remainder of the aspirated tissue in the collection vessel 130. The tapered shape may be generally conical. In certain embodiments, the angle α between the side wall of the upper cap section 142 and the side wall of the lower cap section 140 is between about 5 degrees and about 45 degrees. In other embodiments, the angle α is between about 5 degrees and about 20 degrees.

The collection vessel cap 132 includes a first port 150 and a second port 152 formed therein. A person of skill in the art will appreciate that at least one of the first port 150 and the second port 152 may be formed in the collection vessel 130. In certain embodiments, the first port 150 and the second port 152 are both formed in the upper cap section 142. The first port 150 may be formed in an end of the upper cap section 142 that is opposite the lower cap section 140 where a diameter of the upper cap section 142 is the smallest.

The first port 150 includes a connector that facilitates attachment to another object such as tubing. In certain embodiments, the first port 150 enables to objects to be attached and detached and when the objects are attached, a substantially gas impervious seal is formed. The first port 150 may include a standardized connector profile that enables a variety of objects to be attached thereto. An example of one suitable standardized connector is marketed under the identifier Leur Lock.

The second port 152 may be provided in a spaced-apart relationship from the first port 150 to minimize the potential of the aspirated osteomedullary tissue flowing directly from the second portion 152 to the first port 150 as opposed to being collected in the collection vessel 130. In certain embodiments, the second port 152 is located proximate an intersection of the upper cap section 142 and the lower cap section 140. Similar to the first port 150, the second port 152 may be formed with a standardized connector profile. An example of one such connector profile that can be used for the second port 152 is a tapered push-on connector that facilitates a friction connection. In such embodiments, the push-on connector includes a plurality of ridges, which reduce the potential of the tubing or other object becoming detached from the second port 152.

Because of the challenges in aspirating the bone fragments and osteomedullary tissue that is collected in the collection vessel 130, it is desirable for substantially all of the osteomedullary tissue to be collected into the collection vessel 130 for further processing. The retention of the aspirated osteomedullary tissue in the collection vessel 130 is assisted by a deflector 154 that is positioned on an inner surface of the upper cap section 142 intermediate the first port 150 and the second port 152. The deflector 154 thereby prevents the aspirated osteomedullary tissue from moving directly from the second port 152 to the first port 150. Gravity causes aspirated osteomedullary tissue that contacts the deflector 154 to fall into the collection vessel 130.

Figure 16:
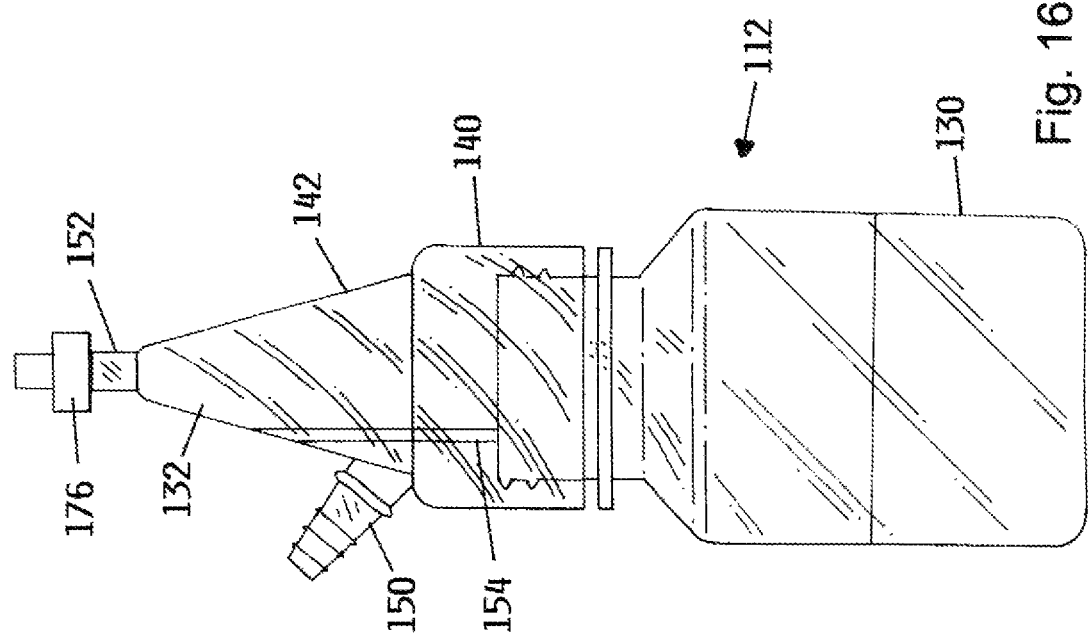
FIG. 16 is a side view of the osteomedullary tissue collection and processing device.

As illustrated in FIG. 16, the deflector 154 may have a generally vertical orientation when the bottom of the collection vessel is on a generally horizontal surface. It is possible for the deflector 154 to have other orientations and/or configurations while producing similar results.

The deflector 154 may be formed with a length that is sufficiently long such that a lower edge of the deflector 154 extends beyond an upper edge of the collection vessel 130 when the collection vessel cap 132 is attached to the collection vessel 130. Such a configuration minimizes the potential of the liquid not dripping into the collection vessel 130.

The deflector 154 may have a width that is greater than the width of the second port 152 to further reduce the potential of aspirated bone fragments and osteomedullary tissue that flow through the second port 152 passing around the deflector 154 as opposed to striking the deflector 154. In certain embodiments, the deflector 154 is at least about 50% wider than the width of the second port 152.

The collection vessel cap 132 may be fabricated from a variety of materials using the concepts of the invention. In one embodiment, at least a portion of the collection vessel cap 132 is fabricated from a transparent material. Such a configuration enables a person using the bone fragment and tissue collection and processing device 112 to view the coagulated red blood cells that are being drained through the first port 150.

Another criterion for the material that is used in fabricating the collection vessel cap 132 is that the material be biologically compatible and facilitate sterilization of the collection vessel cap 132 prior to use. An example of one such material that may be used to fabricate the collection vessel cap 132 is polyethylene terephthalate.

To further reduce the potential of loss of the aspirated bone fragments and tissue that are collected in the osteomedullary tissue collection and processing device 112, a hydrophilic membrane valve 176 may be attached to the first port 150 intermediate the osteomedullary tissue collection and processing device 112 and the vacuum source. The hydrophilic membrane valve 176 allows the vacuum to pull gas therethrough until the hydrophilic membrane becomes wet such as when the osteomedullary tissue collection and processing device 112 is knocked over or the osteomedullary tissue collection and processing device 112 is overfilled with liquid. The hydrophilic membrane valve 176 thereby prevents the bone fragments and aspirated tissue from being drawn out of the bone fragment and tissue collection and processing device 112.

An alternative or additional technique to minimize the potential of aspirated bone fragment and tissue being drawn into the vacuum line may include attaching the bone fragment and tissue collection and processing device 112 to an object proximate to the patient from which the bone fragments and tissue is being aspirated. An example of one suitable option is a clip that attaches the bone fragment and tissue collection and processing device 112 to an IV pole, a drape near the patient or the operating table.

In certain embodiments, an attachment device (not shown) may include a first portion and a second portion. The first portion extends around at least a portion of the collection vessel 130 to engage the collection vessel 130. In certain embodiments, the first portion may include an opening that receives the collection vessel 130. In another embodiment, the first portion extends substantially around the collection vessel 130 proximate to where the collection vessel cap 132 attaches to the collection vessel 130. The second portion includes a clip or similar device that enables the attachment device to be attached to an object in the operating room such as a drape.

Prior to use, the components of the bone fragment and tissue collection and processing device 112 may be sterilized. A person of skill in the art will appreciate that a variety of sterilization techniques may be used. An example of one suitable sterilization technique is exposure of the packaged components to gamma radiation.

As an initial step in harvesting the osteomedullary tissue, the collection vessel cap 132 is attached to the collection vessel 130 so that the bone fragment and tissue collection and processing device 112 looks substantially as illustrated in FIGS. 14 and 15. The bone fragment and tissue harvesting device 114 is attached to the bone fragment and tissue collection and processing device 112 using the tubing 116 so that the system is configured substantially. A vacuum source is attached to the first port 150.

A site is selected from which the bone fragments and tissue is to be harvested. It is possible to use the invention in conjunction with harvesting bone fragments and tissue from a variety of bones in a patient. Preferred sites for harvesting the bone fragments and tissue include the iliac crest and pedicle/vertebral bodies.

A guide wire (not shown) may be used to identify a location at which the needle portion 122 is to be extended into the bone. An imaging technique such as a fluoroscope may be used to assist in the placement and orientation of the guide wire.

The needle portion 122 is extended over the guide wire and into the bone to access the area where the bone fragments and tissue are located. To enhance the volume of bone fragments and tissue that can be aspirated, the needle portion 122 may be pivoted so that the distal end of the needle portion 122 causes bone fragments to be formed. The pivoting of the needle portion 122 also causes morselizing of the osteomedullary tissue. This process significantly increases the volume of beneficial osteomedullary tissue that can be harvested as compared to conventional processing techniques that merely insert the aspiration needle into the bone at different depths.

A vacuum is applied to the system. The person using the system may control application of the vacuum to the needle portion 122 by placing his/her finger over a valve opening 60. When the valve opening 160 is substantially covered, the vacuum is drawn through the needle portion 122 to cause the bone fragments and tissue to be aspirated through the needle portion 122.

The aspirated bone fragments and tissue flows through the tubing 116 and into the bone fragment and tissue collection and processing device 112, where the aspirated bone fragment and tissue accumulate in the collection vessel 130. This process is continued until a desired volume of bone fragment and tissue has been aspirated from the patient.

If it is not possible to obtain a desired volume of the bone fragment and tissue from a particular location, it may be necessary to insert the needle portion 122 into a different location in the bone. It may also be necessary to insert the needle portion 122 into a different bone.

It may be desirable to control the intensity of the vacuum that is pulled through the bone fragment and tissue harvesting device 114. An example of one mechanism to control the vacuum level is using a valve (not shown) that is operably attached to the vacuum line that is attached to the first port 150.

Once a desired amount of bone fragment and tissue is aspirated from the patient, the vacuum line is disconnected from the first port 150 and the tubing 116 is disconnected from the second port 152 and the aspirated bone fragments and tissue are ready for further processing.

Prior to forming bone graft using the aspirated bone fragments and tissue, it may be desirable for the red blood cells to be separated from the other components in the aspirated bone fragments and tissue. One technique that may be used to separate the red blood cells from the other portions of the aspirated bone fragments and tissue is by agglomerating the red blood cells. Once the red blood cells are agglomerated, they become denser than the other materials in the aspirated bone fragments and tissue and thereby settle. An advantage of using the red blood cell agglomerating technique is that it possible to separate a large portion of the red blood cells while minimizing the potential of damage to the other components in the aspirated osteomedullary tissue.

The red blood cells may be caused to agglomerate using a positively charged material. This positively charged material should be relatively inert with respect to the other desirable components in the aspirated tissue such that the positively charged material does not impact the beneficial properties of the aspirated tissue. Furthermore, the positively charged material should have no negative interactions if any of the positively charged material remains in the aspirated tissue, which then becomes incorporated into the bone graft and thereafter is implanted into the patient.

In certain embodiments, the red blood cell agglomerating material is Prepacyte. The red blood cell agglomerating material is added at a volume so that substantially all of the red blood cells in the aspirated tissue are caused to agglomerate.

Figure 17:
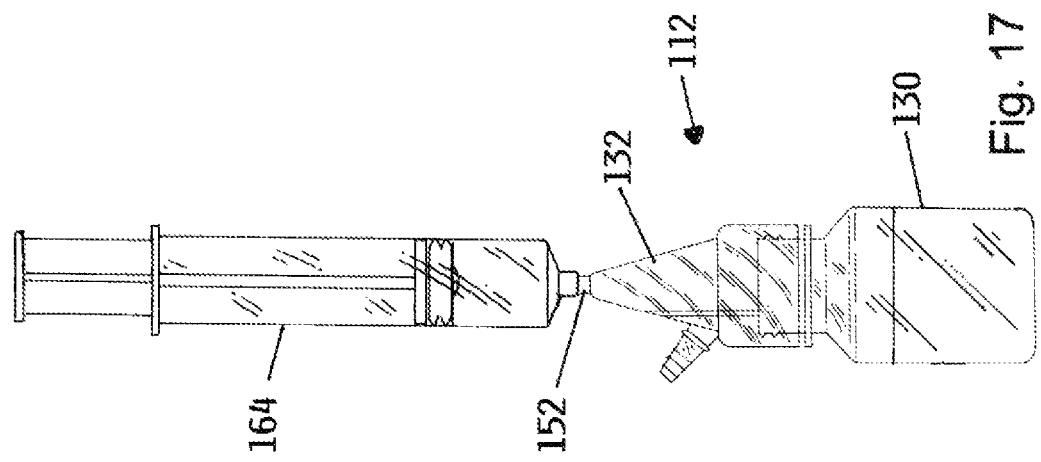
FIG. 17 is a side view illustrating red blood cell coagulating material being injected into aspirated tissue within the osteomedullary tissue collection and processing device.

In certain embodiments, a syringe 164 is attached to the first port 150 and a red blood cell agglomerating material is added to the collection vessel 130, as illustrated in FIG. 17. The second port 152 may be closed with a valve or other mechanism (not shown) that prevents the osteomedullary tissue from spilling through the second port 152.

The time period for substantially all of the red blood cells in the collection vessel 130 to agglomerate may depend on a variety of factors. In certain embodiments, substantially all of the red blood cells agglomerate in less than about 10 minutes after the addition of the red blood cell agglomerating material to the collection vessel 130.

It may be possible to slowly agitate the collection vessel 130 to enhance the dispersal of the red blood cell agglomerating material throughout the aspirated tissue and thereby enhance the rate of the agglomerating process. Once the red blood cells have substantially all agglomerated, the agglomerated red blood cells are allowed to settle in the collection vessel 130.

A first valve 162 is attached to the first port 150, as illustrated in FIG. 18. In certain embodiments, the valve 162 is a stopcock. The osteomedullary tissue collection and processing device 112 is inverted to cause the agglomerated red blood cells to settle into the tapered upper cap section. The valve 162 is opened to drain substantially all of the red blood cells from the osteomedullary tissue collection and processing device 112.

In certain embodiments, the transparent nature of the collection vessel cap 132 facilitates viewing the draining process to maximize the portion of the agglomerated red blood cells that are removed while minimizing loss of the other portions of the aspirated osteomedullary tissue from the osteomedullary tissue collection and processing device 112.

During this process the second port 152 may be closed with a valve or other mechanism 66 that prevents the osteomedullary tissue from spilling through the second port 152. This process enables a large portion of the red blood cells to be removed from the aspirate osteomedullary tissue. As used herein, the term "large portion" means that more than about 90 percent by weight of the red blood cells are separated from the aspirated osteomedullary tissue. In other embodiments, the term "large portion" means that more than about 95 percent by weight of the red blood cells are separated from the aspirated osteomedullary tissue.

The aspirated osteomedullary tissue that remains in the bone fragment and tissue collection and processing device 112 after the removal of the red blood cells can be referred to as a supernatant, which contains substantially all of the desirable constituents present in aspirated osteomedullary tissue.

A benefit of separation of the red blood cells using the process described herein is that the cells that remain in the bone fragment and tissue collection and processing device 112 after the removal of the red bloods cells are substantially unaffected and undamaged in the process of red blood cell aggregation and precipitation.

In certain embodiments, it may be beneficial to concentrate the aspirated osteomedullary tissue prior associating the aspirated osteomedullary tissue with the bone matrix. Such separation technique should facilitate a large portion of the water in the bone marrow aspirate to be separated from the other portions of the bone marrow aspirate. One technique that may be used in the concentration process is centrifugation. Use of a centrifuge is effective at cell concentration but is less desirable in the sterile environment in the operating room where this invention is intended for use.

A filter membrane (not shown) may be provided proximate the outlet port of the cartridge 70 to prevent the osteoconductive matrix from passing out of the cartridge 70. In certain embodiments, the membrane has a particle size of about 250 microns. The membrane will retain the particles having a size of greater than 250 microns. The 250 micron layer will retain the 100 micron particles. The 100 micron layer will retain the 60 micron particles.

It may be desirable to separate non-liquid components in the osteomedullary tissue from liquid components in the osteomedullary tissue that is aspirated with the osteomedullary tissue harvesting device because the non-liquid components may have advantageous characteristics when used in conjunction with bone glue prepared from the osteomedullary tissue. Examples of such non-liquid components include bone chips that are generated by the drilling process to access the interior of the bone. The non-liquid components may also include other tissue from within the bone that is not completely morselized.

To collect the non-liquid components, filter media may be placed inside of the osteomedullary tissue collection device while the osteomedullary tissue is harvested. In certain embodiments, the filter media has sufficiently large pores such that substantially all of liquid in the aspirated osteomedullary tissue flows therethrough. However, the filter media has sufficiently small pores such that substantially all of the non-liquid components in the osteomedullary tissue is retained on the filter media.

In one such embodiment, the filter media is placed proximate the opening in the collection vessel. The filter media may be retained in position with respect to the collection vessel using the collection vessel cap.

During the process of aspirating the osteomedullary tissue, the filter media is placed in the osteomedullary tissue collection device. Thereafter, once the aspiration process is complete, the filter media is removed from the osteomedullary tissue collection device.

The non-liquid components that were retained on the filter media may be mixed into the osteomedullary tissue after the red blood cells are separated therefrom. Alternatively, the non-liquid components may be mixed with the bone graft material prior to the red blood cell depleted osteomedullary tissue being mixed with the bone graft material.

It is also possible to utilize an affinity mechanism to trap desirable cells in the bone matrix. This process may be a preferred retention mechanism as in certain configurations, it is more discriminating for the preferred cells rather than just size. A person of skill in the art will appreciate that a variety of compositions may be utilized based upon the cells that are desired to be trapped in the bone matrix. For example, the attractant composition may exhibit a charge that causes the desired cells to be attracted to the bone matrix.

This attractant composition can be mixed with the bone matrix before the bone matrix is placed into the cartridge. Alternatively, attractant composition can be passed through the osteoconductive matrix after the osteoconductive matrix is placed in the cartridge 170.

The hollow cartridge 170 may be used to mix the red blood cell depleted aspirated osteomedullary tissue and the filtering osteoconductive matrix, e.g., a demineralized bone/extracellular matrix composite. In certain embodiments, the cartridge 170 may have a generally cylindrical shape with an opening that extends between opposite ends thereof, as illustrated in FIG. 19.

Because of the cost and/or challenges associated with obtaining the aspirated osteomedullary tissue and/or the osteoconductive matrix, the interior volume of the cartridge 70 may be selected based upon the amount of bone graft that is desired to be produced. In certain embodiments, the demineralized bone matrix may substantially fill the interior of the cartridge 70 when initially placed therein.

The cartridge 170 may be formed in at least two sections 170a, 170b that are separable to provide access to the bone graft material prepared therein. In one such configuration, the cartridge 170 is formed in two halves that detachably engage each other such as using a screw-type thread mechanism. Alternatively, a cover may be removably attached to at least one end of the cartridge 170.

One end of the cartridge 170 includes a connector that enables the cartridge 170 to be attached to the first port 150. The connection between the first port 150 and the cartridge 170 may be substantially water-tight and facilitate transfer of the aspirated osteomedullary tissue between the osteomedullary tissue collection and processing device 112 and the cartridge 170 in a sterile manner. An example of one suitable connection mechanism is a Leur Lock. An alternative connection mechanism may be utilized a friction fit.

After the cartridge 170 is filled with the desired matrix, the cartridge 170 is attached to the first port 150 and the aspirated osteomedullary tissue is allowed to flow through the first port 150 and then through the matrix in the cartridge 170.

In certain embodiments, the aspirated osteomedullary tissue is allowed to flow through the matrix using gravitational force. In other embodiments, a vacuum may be applied to an end of the cartridge 170 that is opposite the first port 150 to cause the aspirated osteomedullary tissue to be drawn through the matrix. In yet another embodiment, pressure may be applied to the interior of the osteomedullary tissue collection and processing device 112 such as using the second port 152.

To minimize the potential of a channel being formed through the osteoconductive matrix in the cartridge 170, the rate at which the aspirated osteomedullary tissue is passed through the osteoconductive matrix should not be too fast.

Another factor believed to play an important role in distribution of the aspirated osteomedullary tissue throughout the osteoconductive matrix is the use of a relatively consistent rate when the aspirated osteomedullary tissue is passed through the osteoconductive matrix.

A valve 172 may be attached to at least one of the ends of the cartridge 170 to control the flow of the aspirated osteomedullary tissue through the matrix. A person of skill in the art will appreciated that a variety of valves may be selected for such use.

After all of the aspirated osteomedullary tissue has flowed through the osteoconductive matrix in the cylinder 170, the aspirated osteomedullary tissue and the osteoconductive matrix may be sufficiently well mixed such that the resulting bone paste is ready for use. In other situations, additional mixing may be desired to ensure that the bone paste is relatively uniformly mixed.

One option for applying the bone paste is to separate the two sections of the cylinder 170 and then scoop or otherwise remove the bone paste from the cylinder 170. In another configuration, at least one end of the cylinder is detached and a plunger (not shown) is attached to the cylinder 170 so that the bone paste can be dispensed from the cylinder 170 using a mechanism that is similar to a conventional syringe.

Depending on the desired application of the bone paste, the bone paste can be formed with different flowabilities. The flowability of the bone paste can be adjusted by changing the amount of water in the bone marrow aspirate concentrate as well as the amount of water that is allowed to pass through the filter membrane at the second end of the cartridge.

Alternatively to applying the bone graft as a paste, it is possible to form the bone graft material into the desired shape of the implant. After the bone graft material is formed into the desired shape, the moisture content of the bone graft material can be reduced to cause the implant to become more rigid. An example of one technique that may be used to reduce the moisture content of the implant is heating.

The physical properties of the bone graft material may be enhanced by the addition of at least one additive to the bone graft material. An example of one additive is collagen.

The total time from harvesting of the cells from the patient to having a bone graft that is ready for use in the patient can be done in a relatively short period of time. In certain embodiments, the process takes less than one hour. In other embodiments, the process takes between about 30 minutes and about 40 minutes.

In the preceding detailed description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The preceding detailed description, therefore, is not to be taken in a limiting sense, and the scope of the present invention is defined by the appended claims.

It is contemplated that features disclosed in this application, as well as those described in the above applications incorporated by reference, can be mixed and matched to suit particular circumstances. Various other modifications and changes will be apparent to those of ordinary skill.

The invention claimed is:

1. A tissue collection and processing system for collecting bone fragments and tissue aspirated from a bone, wherein the tissue collection and processing system comprises:
  a collection vessel having an opening formed therein to receive bone fragments and tissue aspirated from the bone;
  a collection vessel cap, wherein the collection vessel cap or the collection vessel comprises a first port;
  a bone fragment and tissue harvesting device that is capable of aspirating bone fragments and tissue from the bone;
  a first tubing that fluidly connects the bone fragment and tissue harvesting device to the first port;
  a processing piston having an upper surface and a lower surface, wherein processing piston comprises a connection port and a bore, wherein the connection port is proximate the upper surface, wherein the bore is fluidly connected to the connection port and extends toward the lower surface and wherein the processing piston has a density that is less than a density of fluid in the aspirated bone fragments and tissue;
  a second tubing; and
  a fluid withdrawal mechanism that is fluidly connected to the connection port with the second tubing to withdraw the fluid from the collection vessel, wherein the tissue collection and processing system is operable in a first configuration and a second configuration, wherein when in the first configuration, the collection vessel cap engages the collection vessel to substantially seal the opening and wherein when in the second configuration, the processing piston is placed in the collection vessel opening and wherein as fluid is withdrawn from the collection vessel, the processing piston is slidable in the collection vessel opening.

2. The tissue collection and processing system of claim 1, wherein the processing piston has a side profile that conforms to a shape of the opening.

3. The tissue collection and processing system of claim 1, wherein the collection vessel has an upper end and a lower end and wherein the processing piston is substantially restricted to moving between the upper end and the lower end.

4. The tissue collection and processing system of claim 1, wherein the processing piston is substantially hollow.

5. The tissue collection and processing system of claim 1, wherein at least a portion of the collection vessel and the first tubing is transparent.

6. The tissue collection and processing system of claim 1, wherein the fluid withdrawal mechanism is a syringe.

7. The tissue collection and processing system of claim 1, and further comprising a filter container that is capable of separating bone fragments from the aspirated bone fragments and tissue, wherein the filter container is mounted with respect to the first port.

8. The tissue collection and processing system of claim 7, wherein the filter container is attached to the collection vessel cap so that the filter container is in the opening when the collection vessel cap is in engagement with the collection vessel.

9. A tissue collection and processing system for collecting bone fragments and tissue aspirated from a bone, wherein the tissue collection and processing system comprises:
  a collection vessel having an opening formed therein to receive bone fragments and tissue aspirated from the bone;
  a collection vessel cap, wherein the collection vessel cap or the collection vessel comprises a first port;
  a bone fragment and tissue harvesting device that is capable of aspirating bone fragments and tissue from a bone;
  a first tubing;
  a filter container mounted with respect to the first port, wherein the first tubing fluidly connects the bone fragment and tissue harvesting device to the first port so that a portion of the bone fragments and tissue in the aspirated bone fragments that are not retained in the filter container accumulate in the collection vessel;
  a processing piston having an upper surface and a lower surface, wherein processing piston comprises a connection port and a bore, wherein the connection port is proximate the upper surface, wherein the bore is fluidly connected to the connection port and extends toward the lower surface and wherein the processing piston has a density that is less than a density of fluid in the aspirated bone fragments and tissue;
  a second tubing; and
  a fluid withdrawal mechanism that is fluidly connected to the connection port with the second tubing to withdraw the fluid from the collection vessel, wherein the tissue collection and processing system is operable in a first configuration and a second configuration, wherein when in the first configuration, the collection vessel cap engages the collection vessel to substantially seal the opening and wherein when in the second configuration, the processing piston is placed in the collection vessel opening and wherein as fluid is withdrawn from the collection vessel, the processing piston is slidable in the collection vessel opening.

10. The tissue collection and processing system of claim 9, wherein the filter container is mounted to the collection vessel cap so that the filter container is in the opening when the collection vessel cap is in engagement with the collection vessel.

11. The tissue collection and processing system of claim 10, wherein at least a portion of the filter container is detachably mounted to an inner surface of the collection vessel cap.

12. The tissue collection and processing system of claim 9, wherein the filter container is capable of providing mechanical separation and affinity separation of the bone fragments and tissue.

13. A method of collecting and processing bone fragments and tissue aspirated from a bone, wherein the method comprises:
  providing a collection vessel, a collection vessel cap and a filter container, wherein the collection vessel has an opening formed therein, wherein the collection vessel or the collection vessel cap comprises a first port;
  mounting the filter container with respect to the first port;
  attaching the collection vessel cap to the collection vessel to substantially seal the opening;
  connecting the first port to a bone fragment and tissue harvesting device with a first tubing;
  aspirating bone fragments and tissue from a bone with the bone fragment and tissue harvesting device;
  retaining substantially all of the bone fragments in the filter container;
  accumulating the aspirated tissue that is not retained in the filter container in the collection vessel;
  detaching the collection vessel cap from the collection vessel;

positioning a processing piston in the opening, wherein the processing piston has an upper surface and a lower surface, wherein processing piston comprises a connection port and a bore, wherein the connection port is proximate the upper surface, wherein the bore is fluidly connected to the connection port and extends toward the lower surface and wherein the processing piston has a density that is less than a density of fluid in the aspirated bone fragments and tissue;

fluidly connecting a fluid withdrawal mechanism to the connection port with a second tubing;

withdrawing the aspirated tissue from the collection vessel using the fluid withdrawal mechanism; and sliding the processing piston in the collection vessel opening as the aspirated tissue is withdrawn from the collection vessel.

14. The method of claim 13, and further comprising forming a bone void filler with the portion of the bone fragments and tissue retained in the filter container.

15. The method of claim 13, and further comprising mounting the filter container to the collection vessel cap so that the filter container is in the opening when the collection vessel cap is in engagement with the collection vessel.

16. The method of claim 15, wherein at least a portion of the filter container is detachably mounted to an inner surface of the collection vessel cap.

17. The method of claim 13, wherein at least one of mechanical separating and affinity separating cause the at least a portion of the bone fragments and tissue to be retained in the filter container.

18. The method of claim 13, wherein the bone fragments and tissue are aspirated from the bone using a vacuum that is applied to a second port on the collection vessel cap or the collection vessel.

* * * * *